US012371407B2

(12) United States Patent
Verduyckt et al.

(10) Patent No.: US 12,371,407 B2
(45) Date of Patent: Jul. 29, 2025

(54) PROCESS FOR THE RECOVERY OF EPSILON-CAPROLACTAM FROM NYLON 6-CONTAINING MULTI-COMPONENT MATERIAL

(71) Applicant: CAP III B.V., Urmond (NL)

(72) Inventors: Jasper Verduyckt, Urmond (NL); Marijke Hilde Leen Groothaert, Urmond (NL); Anna Dite Cuiper, Urmond (NL); Wenjing Fu, Urmond (NL); Johan Thomas Tinge, Urmond (NL)

(73) Assignee: CAP III B.V., Urmond (NL)

( * ) Notice: Subject to any disclaimer, the term of this patent is extended or adjusted under 35 U.S.C. 154(b) by 0 days.

(21) Appl. No.: 18/832,297

(22) PCT Filed: Jan. 27, 2023

(86) PCT No.: PCT/EP2023/052067
§ 371 (c)(1),
(2) Date: Jul. 23, 2024

(87) PCT Pub. No.: WO2023/144337
PCT Pub. Date: Aug. 3, 2023

(65) Prior Publication Data
US 2025/0100974 A1    Mar. 27, 2025

(30) Foreign Application Priority Data

Jan. 28, 2022  (EP) .................................... 22154093
Nov. 21, 2022  (EP) .................................... 22208656

(51) Int. Cl.
C07D 201/12    (2006.01)
C07D 201/16    (2006.01)
C07D 223/10    (2006.01)
C08J 11/12     (2006.01)
C08J 11/14     (2006.01)
C08J 11/16     (2006.01)

(52) U.S. Cl.
CPC .................................. C07D 223/10 (2013.01)

(58) Field of Classification Search
CPC .. C07D 201/12; C07D 201/16; C07D 223/10; C08J 11/12; C08J 11/14; C08J 11/16; Y02W 30/62
See application file for complete search history.

(56) References Cited

U.S. PATENT DOCUMENTS

| 5,169,870 A | 12/1992 | Corbin et al. |
| 5,233,037 A | 8/1993 | Nielinger et al. |
| 5,869,654 A | 2/1999 | Sifniades et al. |
| 5,929,234 A | 7/1999 | Sifniades et al. |
| 5,948,908 A | 9/1999 | Sifniades et al. |
| 5,977,193 A | 11/1999 | Corbin et al. |
| 5,990,306 A | 11/1999 | Mayer et al. |
| 6,448,395 B1 | 9/2002 | Simons et al. |
| 2002/0038022 A1 | 3/2002 | Agterberg et al. |
| 2014/0255255 A1 | 9/2014 | Heilberg |

FOREIGN PATENT DOCUMENTS

| CN | 1196048 A | 10/1998 |
| CN | 1278792 A | 1/2001 |
| CN | 1332158 A | 1/2002 |
| CN | 1793124 A | 6/2006 |
| CN | 103467378 A | 12/2013 |
| CN | 107418198 A | 12/2017 |
| DE | 4211609 A1 | 3/1993 |
| DE | 10048824 A1 | 4/2002 |
| EP | 603434 A1 | 6/1994 |
| EP | 670 308 A1 | 9/1995 |
| EP | 0627417 B1 | 8/1999 |
| EP | 1 173 419 A1 | 1/2002 |
| GB | 1157416 A | 7/1969 |
| GB | 2085432 A | 4/1982 |
| JP | H0848666 A | 2/1996 |
| JP | H10298162 A | 11/1998 |
| JP | 2000038471 A | 2/2000 |
| JP | 2000178249 A | 6/2000 |
| JP | 2007099645 A | 4/2007 |
| JP | 2008031127 A | 2/2008 |
| JP | 2008031128 A | 2/2008 |
| JP | 2008031388 A | 2/2008 |
| JP | 2008179816 A | 8/2008 |
| JP | 2008239985 A | 10/2008 |
| JP | 2011088943 A | 5/2011 |
| KR | 20110068001 A | 6/2011 |

(Continued)

OTHER PUBLICATIONS

Machine translation of JP 2000-178249 (Year: 2000).*
U.S. Appl. No. 18/832,305, filed Jul. 23, 2024, Jasper Verduyckt et al.
U.S. Appl. No. 18/832,315, filed Jul. 23, 2024, Jasper Verduyckt et al.
International Search Report and Written Opinion issued in related PCT Application No. PCT/EP2023/052067, dated Apr. 11, 2023.
Tinge et al. (2018). Caprolactam. In Ullmann's Encyclopedia of Industrial Chemistry. May 25, 2018. https://doi.org/10.1002/14356007.a05_031.pub3.

(Continued)

Primary Examiner — Brenda L Coleman
(74) Attorney, Agent, or Firm — Honigman LLP

(57) ABSTRACT

The present invention provides an improved process for the recovery of ε-caprolactam from Nylon 6 comprising multi-component material, in particular multi-layered film. Further, the invention provides a plant configured to carry out the process of the invention, and the recovered e-caprolactam obtainable by the process of the invention that has a product carbon footprint of less than 2.5 kg $CO_2$ equivalent per kg purified e-caprolactam (based on data originating from ecoinvent version 3.7.1; location: Europe).

20 Claims, 2 Drawing Sheets

(56) References Cited

FOREIGN PATENT DOCUMENTS

| WO | 97/03048 | A1 | 1/1997 |
| WO | 9720813 | A1 | 6/1997 |
| WO | 9911616 | A1 | 3/1999 |
| WO | 2021021031 | A1 | 2/2021 |
| WO | 2022/115602 | A1 | 6/2022 |
| WO | 2022/129022 | A1 | 6/2022 |

OTHER PUBLICATIONS

Herzog et al. (2013). Polyamides. In Ullmann's Encyclopedia of Industrial Chemistry, (Ed.). Jan. 15, 2013. https://doi.org/10.1002/14356007.a21_179.pub3.

Dmitrieva et al., "Regeneration of Epsilon-Caprolactam From Wastes In the Manufacture of Polycaproamide Fibres and Yarns", Fibre Chemistry, pp. 229-241, Mar. 1986, (translated from Khimicheskie Volokna, No. 4, pp. 5-12, Jul.-Aug. 1985).

A. A. Ogale, "Depolymerization of Nylon 6: Some Kinetic Modeling Aspects", Journal of Applied Polymer Science, vol. 29, 1984, pp. 3947-3954, https://doi.org/10.1002/app.1984.070291227.

Synowiec et al. "Industrial Purification of Caprolactam by Means of Crystallization from Aqueous Solutions", Crystal Research and Technology, vol. 18, noi. 7, Jan. 1, 1983 (Jan. 1, 1983), pp. 951-957.

International Search Report and Written Opinion issued in related PCT Application No. PCT/EP2023/052071, dated May 4, 2023.

International Search Report and Written Opinion issued in related PCT Application No. PCT/EP2023/052069, dated Apr. 11, 2023.

U.S. Appl. No. 18/992,408, filed Jan. 8, 2025, Jasper Verduyckt et al.

U.S. Appl. No. 18/992,440, filed Jan. 8, 2025, Jasper Verduyckt et al.

Office Action issued in related Korean Patent Application No. 10-2024-7028713, dated Dec. 12, 2024.

International Search Report and Written Opinion issued in related PCT Application No. PCT/EP2023/069235, dated Aug. 7, 2023.

Gong Caihong et al: "Simple process for separation and recycling of nylon 6 and polyurethane components from waste nylon 6/polyurethane debris", Textile Research Journal, vol. 91, No. 1-2 Jun. 17, 2020 (Jun. 17, 2020), pp. 18-27, XP093006676, GB ISSN: 0040-5175, DOI: 10.1177/0040517520931893 Retrieved from the Internet: URL:http://journals.sagepub.com/doi/full-x ml/10.1177/0040517520931893 Title, Abstract, Scheme 1, p. 19, right, lines 11-13 and lines 17-18, Figure 4 (IR) for nylon and Figure 6 (NMR) for the urethane, p. 23, right, lines 37-39.

Yin Yunjie et al: "Removal of spandex from nylon/spandex blended fabrics by selective polymer degradation", Textile Research Journal vol. 84, No. 1 May 21, 2013 (May 21, 2013), pp. 16-27, XP093006635, GB ISSN: 0040-5175, DOI: 10.1177/0040517513487790 Retrieved from the Internet:URL:http://journals.sagepub.com/doi/full-xml/10.1177/0040517513487790p17, left, lines 14-18.

International Search Report and Written Opinion issued in related PCT Application No. PCT/EP2023/069236, dated Sep. 12, 2023.

Office Action issued in related Chinese Application No. 202380019033.8, dated Mar. 3, 2025.

Office Action issued in related Chinese Patent Application No. 202380019025.3, dated May 20, 2025.

\* cited by examiner

FIG. 2
FIG. 2a
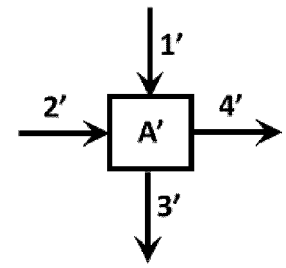
FIG. 2b
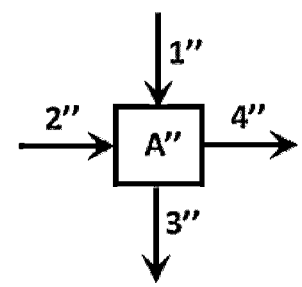
FIG. 2c
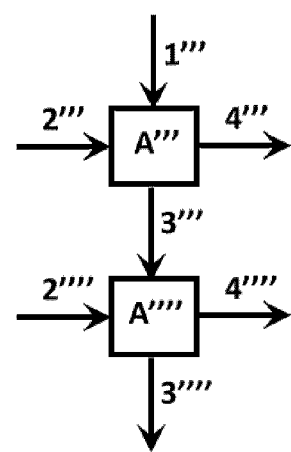

PROCESS FOR THE RECOVERY OF EPSILON-CAPROLACTAM FROM NYLON 6-CONTAINING MULTI-COMPONENT MATERIAL

CROSS-REFERENCE TO RELATED APPLICATIONS

This application is a national phase entry of PCT Application No. PCT/EP2023/052067 filed Jan. 27, 2023, which claims the benefit under 35 U.S.C. § 119(e) to European Patent Application Nos. EP 22154093.3, filed Jan. 28, 2022, and EP 22208656.3, filed on Nov. 21, 2022. The disclosures of those priority applications are incorporated by reference herein in their entireties.

FIELD OF THE INVENTION

The present invention relates to a process for the recovery of epsilon-caprolactam derived from a Nylon 6 comprising multi-component material, in particular multi-layered film. Further, the invention relates to a plant configured to carry out the process of the invention and to the recovered epsilon-caprolactam obtainable by the process of the invention.

BACKGROUND OF THE INVENTION

In 1938, Paul Schlack invented Nylon 6 (CAS Number: 25038-54-4), also known as polyamide 6, poly(caprolactam), poly(hexano-6-lactam), poly(6-aminohexanoic acid), poly(hexamethylene adipamide) or poly[imino(1-oxohexane-1,6-diyl)].

Generally, Nylon 6 is synthesized by ring-opening polymerization of epsilon-caprolactam at a temperature of about 260° C. in an inert atmosphere:

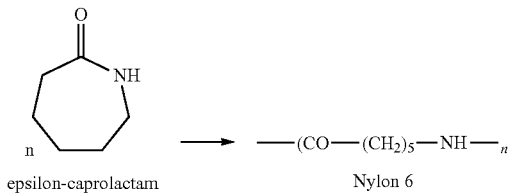

Processes for the production of virgin epsilon-caprolactam are described in, e.g., Chapter 25 "Caprolactam", in Ullmann's Encyclopedia of Industrial Chemistry (May 25, 2018), Wiley-VCH Verlag GmbH & Co. KGaA, Weinheim, Germany, electronically available via https://doi.org/10.1002/14356007.a05_031.pub3.

Processes for the production of nylon 6 are described in, e.g., Chapter "Polyamides", in Ullmann's Encyclopedia of Industrial Chemistry (Jan. 15, 2013), Wiley-VCH Verlag 30 GmbH & Co. KGaA, Weinheim, Germany, electronically available via https://doi.org/10.1002/14356007.a21_179.pub3.

Nowadays, Nylon 6 is worldwide the most produced synthetic polyamide and has a variety of favorable properties for industrial applications, including high mechanical strength, in particular stiffness, hardness and toughness, good electrical insulating properties, good dyeability, good processability, good UV light protection, good fatigue resistance and good barrier functions for gases, aromas, hydrocarbon solvents and low polarity aroma substances from food. This favorable set of properties is the reason why Nylon 6 is used intensively in very different industries such as building and construction, consumer goods, electronics and electricals, transportation and packaging. A disadvantage of the use of Nylon 6, however, is that it is more expensive than the polyolefins polyethylene and polypropylene. Polyolefins, in turn, have the disadvantage that they are more limited in their industrial applicability due to their poor gas barrier functions, their low temperature resistance and their difficult bonding properties.

As a result, Nylon 6 is extensively used as a component in multi-component materials, in most cases in combination with polyolefins. Particularly relevant Nylon 6-comprising multi-component materials are, e.g., flexible modified atmosphere or controlled atmosphere packaging films which are usually employed to maintain a certain atmosphere inside food-containing packages to improve the shelf life of the packaged products. The majority of today's packaging films are multi-layer films, which typically comprise from two to 15, but can also comprise many more layers. An example of an 11-layer co-extruded cast film is the following: Nylon 6/TIE/PE(1)/TIE/Nylon 6/EVOH/PA/TIE/PE(2)/PE(3)/PE(4) wherein TIE is a tie layer, EVOH is ethylene vinyl alcohol, PA is a polyamide other than Nylon 6, and PE(1), PE(2), PE(3) and PE(4) are different grades of polyethylene. The typical purpose of using Nylon 6 in such multi-component materials is to confer mechanical strength and puncture resistance properties and/or barrier properties to restrict gas exchange and loss of aromas. Nylon 6-containing multi-layer films in particular allow maintaining an optimized modified atmosphere inside the package, especially a certain oxygen concentration which is key, for example, to preserve the freshness of fresh products for a longer period of time. The use of multi-layer films can enable cost reductions since cheaper polymers can partially replace the more expensive polymers such as Nylon 6. Nylon 6 is also an excellent substitute for aluminum and other metal films.

Multi-component materials comprising more than one (polymer) component are attractive for industrial applications because, e.g., alternative layering of two (or more) different components is a way to obtain composite materials with new properties compared to the pure components. The combination of several layers of different materials can, e.g., improve the mechanical and physical properties of films including puncture, tear and heat resistance as well as moisture and gas (in particular oxygen) barrier properties. Since it is possible to monitor continuously how the properties of the multi-component material change upon altering the employed components and the thickness of the employed component layers, new composite materials with desired properties can be developed relatively easily.

In multi-component materials, in particular multi-layer films, polyolefin layers are often combined with layers made up of polar polymers, like Nylon 6, Nylon 66, EVOH (ethylene vinyl alcohol) or PVDC (polyvinylidene chloride). In addition, tie layers comprising special adhesive polymers or tie resins (e.g., polyurethanes and acid/anhydride grafted polyolefins) are typically required as intermediate layers between two dissimilar components that do not adhere well. As explained above, use of Nylon 6 in multi-component materials has become very common to improve the mechanical and gas barrier properties of such materials. Another important reason, why Nylon 6 is often combined with other materials is the cost saving on the rather costly Nylon 6.

Environmental concerns regarding the production and the usage of these multi-component Nylon 6-containing materials relate to the in-process and the post-consumer generated wastes. These concerns could be mitigated by recycling individual components, such as Nylon 6, from multi-component materials that are no longer used or disposed. As packaging materials, Nylon 6-containing multi-layer films are a particularly relevant source of waste. These often contain Nylon 6 in significant amounts. Thus, if a feasible process existed for recovering Nylon 6 from these composite waste materials, this would not only benefit the environment, but also present an economically valuable new source of Nylon 6.

The same applies for in-process wastes generated in processes using Nylon 6, in particular film production processes. For a limited number of applications, these wastes can be recovered and reused as regrind. However, the optical and mechanical properties of the material are negatively impacted by the regrind, and further deterioration occurs every time the cycle of reuse and processing is repeated. As a result, the cycle of reuse and processing cannot be repeated as often as desired.

In addition, Nylon 6 that is recycled according to currently existing methods is generally not rated as "food grade plastic", which limits the applications to a large extent.

Mechanical recycling (a.k.a. material recycling or back-to-plastics recycling or regrinding) refers to operations that aim to recover plastics via mechanical processes (grinding, washing, separating, drying, re-granulating and compounding), thus producing recyclates that can be converted into plastics products, substituting virgin plastics. Currently, most virgin plastics are produced from a petrochemical feedstock, such as natural gas, coal or crude oil, which has never been used or processed before. In mechanical recycling processes, the polymer chain remains more or less intact. Mechanical recycling is a form of downcycling of the waste because the recycled material is of lower quality and functionality than the original material.

Depolymerization or chemical recycling is a technology in which the polymer is converted into its monomer components (epsilon-caprolactam in case the polymer is Nylon 6). The specifications of the recovered monomer determines whether it can substitute virgin monomers for all or just a limited amount of applications. Virgin monomers are produced from a petrochemical feedstock, such as natural gas, coal or crude oil, which has never been used or processed before.

Next to regrinding Nylon 6-comprising materials, processes for depolymerizing Nylon 6 to its valuable monomer, epsilon-caprolactam, have been developed. These typically use Nylon 6 plastic articles as starting materials, that are produced, for example, by injection moulding, extrusion, spinning or other processing steps.

Depolymerization of Nylon 6 into epsilon-caprolactam is the reverse reaction of the ring-opening polymerization of epsilon-caprolactam:

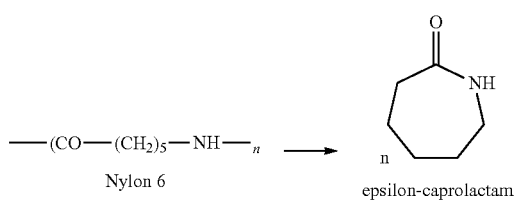

Processes for depolymerization of Nylon 6 are known. Such processes might be operated in a batch-wise operated mode, in a semi-continuous mode (in general with batch-wise (re)charging of Nylon 6 to the depolymerization reactor) or in a continuous mode.

L. A. Dmitrieva, A. A. Speranskii, S. A. Krasavin and Y. N. Bychkov, "Regeneration of epsilon-caprolactam From Wastes In the Manufacture of Polycaproamide Fibres and Yarns", Fibre Chemistry, pp. 229-241, March 1986, (translated from Khimicheskie Volokna, No. 4, pp. 5-12, July-August, 1985) is a literature review describing processes for depolymerizing Nylon 6 with and without using a catalyst.

A. A. Ogale, "Depolymerization of Nylon 6: Some Kinetic Modeling Aspects", Journal of Applied Polymer Science, vol. 29, 1984, pp. 3947-3954, electronically available via https://doi.org/10.1002/app.1984.070291227 is a paper describing the depolymerization kinetics of Nylon 6.

Generally, the prior art of chemical regeneration or recycling processes that depolymerize essentially pure Nylon 6 into epsilon-caprolactam monomers comprise a hydrolytic degradation step at elevated temperature in the presence of water and a reclaiming step of the formed monomer by steam distillation. The hydrolytic degradation step can be performed in both the presence and the absence of a catalyst. As catalyst, both acidic compounds, such as, e.g., phosphoric acid and boric acid, as well as basic compounds, such as, e.g., potassium carbonate and sodium hydroxide, can be used.

U.S. Pat. No. 5,929,234 describes a process for the recovery of epsilon-caprolactam from polycaprolactam-containing waste material. The depolymerization is performed in the absence of added catalyst with superheated steam at a temperature of about 250° C. to about 400° C. and at a pressure within the range of about 1 atm to about 100 atm and substantially less than the saturated vapor pressure of water at the temperature wherein an ε-caprolactam-containing vapor stream is formed.

Reclaiming of epsilon-caprolactam from essentially pure Nylon 6 by recovering extraction liquid in Nylon 6 polymerization plants, recycling Nylon 6 scrap (i.e., Nylon 6 polymer that is substantially free of non-Nylon 6 materials) or products made of almost pure Nylon 6 (e.g., fishing nets) has been known for a long time.

For example, DE4211609 discloses a process for the recovery of epsilon-caprolactam by thermal cleavage of polyamide 6 in the presence of small amounts of potassium carbonate at 250-320° C. and a process for the purification of the recovered epsilon-caprolactam. DE4211609 describes that the process is not only applicable to pure polyamide 6 products, but also to glass fiber-containing and filler-containing polyamide 6 products, as well as to products containing impact modifiers. "Polyamide 6" as used by DE4211609 refers to pure polyamide 6 as well as polyamides, which are preferably based on polyamide 6 to more than 80% by weight.

CN103467378 discloses a process for producing epsilon-caprolactam by using recovered waste chinlon silks and leftovers, wherein phosphoric acid is used as a catalyst for depolymerization. Superheated steam is charged into the reaction system during the depolymerization process.

U.S. Pat. No. 5,869,654 discloses a process for the recovery of epsilon-caprolactam from polycaprolactam processing waste, wherein the polycaprolactam can be selected from scrap Nylon 6 polymeric and/or oligomeric materials such as yarn waste, chip waste or extruder slag. The process comprises the step of: in the absence of added catalyst, contacting the polycaprolactam waste with superheated steam at a temperature of about 250° C. to about 400° C. and at a pressure within the range of about 1.5 atm to about 100 atm and substantially less than the saturated vapor pressure of water at the temperature wherein an epsilon-caprolactam-containing vapor stream is formed.

JP2000038471 discloses a process for depolymerizing a Nylon 6 resin from moulded bodies to obtain epsilon-caprolactam, in particular the depolymerization of automotive resin parts such as Nylon 6 fastener parts, electrical parts, body mechanism parts and exterior parts, in which Nylon 6 accounts for 90% by weight or more of the total organic compounds in the moulded body.

Although processes for the depolymerization of almost pure waste Nylon 6 to its valuable monomer, epsilon-caprolactam, have been developed, recovering epsilon-caprolactam from Nylon 6-containing multi-component materials, especially such with moderate to high Nylon 6 contents (e.g., 40 wt. % to 80 wt. %), is still a big challenge. Recovering epsilon-caprolactam from Nylon 6-containing multi-component materials with low Nylon 6 contents (e.g., less than 40 wt. %) is even more difficult. A Nylon 6-containing product with moderate to high Nylon 6 content is, e.g., carpet. High quality carpets typically comprise up to 55 wt. % Nylon 6-containing face fiber. The remainder are backing (support) materials.

Reclaiming epsilon-caprolactam from Nylon 6-containing materials with low and even moderate to high Nylon 6 contents has not been commercially feasible or successful based on the existing methods.

Most commonly reported issues related to the recovery of epsilon-caprolactam from Nylon 6-containing materials with moderate to high Nylon 6 contents are low recovery yields. This low recovery yield is on the one hand due to difficulties in separating the formed epsilon-caprolactam from the non-Nylon 6 materials. On the other hand, the low recovery yield is due to decomposition reactions which lead to the production of ammonia and due to the inhomogeneity of the depolymerization mixture since effective mixing is prevented due to the high viscosity of the depolymerization mixture so that local overheating and high consumption figures of expensive superheated steam (used as a stripping agent) occur.

The introduction of a mechanical pre-treatment step (e.g., shaving of the face fiber from the backing of the carpet or grinding followed by density separation, like sink-float separation and wind-sifting) allows to produce feedstocks of processed carpet material containing more than 90 wt. % of Nylon 6, which can be used in the above-described prior art depolymerization processes. This mechanical pre-treatment is, however, mainly applied to off-spec material inside carpet and other Nylon 6-based textile production facilities (pre-consumer wastes). It is also not transferrable to other, non-carpet Nylon 6-comprising multi-component materials.

Currently, no processes are available to recover high purity epsilon-caprolactam from Nylon 6 comprising multi-component materials in an economically reasonable manner despite the urgent need for such processes. In particular, there is an urgent need for epsilon-caprolactam recovery processes that will work with more demanding Nylon 6 comprising multi-component materials, e.g., such that have low to medium high Nylon 6 contents (e.g., from 1 wt. % up to 35 wt. %) and for recovery of epsilon-caprolactam from complex Nylon 6-containing multi-component products that cannot be pre-concentrated by a simple mechanical pre-treatment step (like shaving or grinding, followed by density separation). Finally, there is a need for processes that allow the recovery of epsilon-caprolactam from Nylon 6 comprising multi-component materials, like multi-layer films, in which Nylon 6 layers are often sandwiched between non-Nylon 6 components and therefore not accessible from the outer-surface of these materials).

Taken together, prior art processes for the recovery of epsilon-caprolactam from Nylon 6-containing multi-component materials are not able to produce high quality epsilon-caprolactam grades that can be used to replace virgin epsilon-caprolactam grades for high demanding applications.

Currently, no processes are available to recover high purity epsilon-caprolactam from Nylon 6-containing multi-component materials despite the urgent need for such processes. In particular, there is an urgent need for high purity epsilon-caprolactam recovery processes that can replace virgin epsilon-caprolactam grades for high demanding applications, like for high speed melt spinning during textile fiber production.

Further, there is a need for processes that allow the recovery of high purity epsilon-caprolactam from Nylon 6-containing multi-component materials in an economically reasonable manner. The production costs of the recovered high purity epsilon-caprolactam should be in the same ballpark or lower than the production costs of virgin high purity epsilon-caprolactam.

And there is a need to purify the crude epsilon-caprolactam obtained by depolymerization of Nylon 6-containing multi-component materials without using oxidation agents like potassium permanganate ($KMnO_4$) or adsorbents like (activated) carbon and kieselguhr. Technologies that are based on these oxidation agents and adsorbents are quite laborious and produce solid wastes.

Furthermore there is a need to provide high purity grade epsilon-caprolactam from Nylon 6-containing multi-component materials that has a significantly lower carbon footprint than the epsilon-caprolactam obtained via new synthesis, e.g., by Beckmann rearrangement of virgin cyclohexanone oxime.

Finally, there is a need for processes that allow the recovery of epsilon-caprolactam from Nylon 6-containing multi-component materials on an industrial scale in order to process the huge amounts of nylon 6-containing multi-component materials that are wasted annually.

SUMMARY OF THE INVENTION

It is an object of the present invention, to satisfy one or more of the above-described needs and to overcome the disadvantages associated with the prior art methods.

In particular, it is an object of the present invention to provide a process for recovering high purity epsilon-caprolactam from Nylon 6 comprising multi-component waste materials in an economically responsible manner and with high recovery yields. It is in particular an object of the present invention to provide a process that is suitable to recover epsilon-caprolactam from Nylon 6-containing multi-component waste materials having Nylon 6 contents up to 35 wt. % as well as from complex Nylon 6-containing multi-component materials, in particular Nylon 6-containing multi-layer films.

It is also an object of the present invention to provide a process for recovering high purity epsilon-caprolactam derived from a Nylon 6-containing multi-component material that can replace high purity virgin epsilon-caprolactam for all applications including high speed melt spinning of Nylon 6 for the production of thin textile fibers.

It is a further object of the invention to provide a process for recovering high purity grade epsilon-caprolactam from Nylon 6-containing multi-component waste materials which is characterized by a significantly lower carbon foot print than a process for producing epsilon-caprolactam via new synthesis, e.g., by Beckmann rearrangement of cyclohexanone oxime.

The invention therefore also aims to provide a process that reduces the environmental burden of Nylon 6 comprising multi-component waste materials and products made therefrom.

All or at least some of the aforementioned objects are solved by the process of claims 1 and 15, the plant of claim 13 and/or the product of claim 14.

Surprisingly, it was found that high purity grade epsilon-caprolactam can be obtained in high yields from Nylon 6-containing multi-component materials by the following process of the invention. The process of the invention makes use of a plant that comprises (A) a Nylon 6-pre-concentration section, (B) a depolymerization section, (C) a recovery section, and (D) a purification section. The process of the invention comprises the steps:
a) extracting the Nylon 6-containing multi-component material in the Nylon 6-pre-concentration section with one or more organic solvents to obtain a solid pre-concentrated Nylon 6-containing material, which is enriched in Nylon 6 as compared to the Nylon 6-containing multi-component material;
b) depolymerizing the pre-concentrated Nylon 6-containing material in the depolymerization section in the presence of water to obtain a vapor stream comprising water and epsilon-caprolactam in a weight to weight ratio of 2:1 to 15:1;
c) recovering crude epsilon-caprolactam from said vapor stream in the recovery section; and
d) purifying said crude epsilon-caprolactam in the purification section to obtain purified epsilon-caprolactam.

It was surprising that combining the special sequence of processing steps and process conditions according to the invention, i.e., the sequence of the above-defined Nylon 6 pre-concentration, depolymerization, recovery and purification steps, allows to recover high grade epsilon-caprolactam from Nylon 6-containing multi-component material in high yields and in a straight-forward and economically reasonable manner. The process of the invention is economically reasonable and advantageous from several points of view. Firstly, the process of the invention is suitable for a large variety of Nylon 6-containing multi-component materials that can, e.g., differ in their overall composition, in their Nylon 6-content and/or in the distribution of Nylon 6 within the material. Secondly, the process of the invention allows to effectively separate Nylon 6 from non-Nylon 6 compounds so that high purity grade epsilon-caprolactam can be obtained. Thirdly, the extraction of Nylon 6 from the Nylon 6-containing multi-component material by the process of the invention is so effective that epsilon-caprolactam can be obtained in high yields. Lastly, the process of the invention allows to produce epsilon-caprolactam with a significantly lower carbon foot print compared to epsilon-caprolactam produced by de novo synthesis of epsilon-caprolactam, e.g., by the Beckmann rearrangement of cyclohexanone oxime. The process of the invention allows to process waste Nylon 6-containing multi-component material efficiently and to reduce the environmental burden of said products. In particular, the process of the invention allows the production of purified epsilon-caprolactam with a carbon foot print of less than 2.5 kg $CO_2$ equivalent per kg purified epsilon-caprolactam, which is a substantial improvement compared to the 7.5 to 6.5 kg $CO_2$ eq./kg epsilon-caprolactam traditionally associated with the production of "virgin" epsilon-caprolactam obtained from a Beckmann rearrangement of cyclohexanone oxime (based on data originating from ecoinvent version 3.7.1; location: Europe). Values for product carbon footprint stated herein are, unless otherwise stated, based on data originating from ecoinvent version 3.7.1 and Europe as location.

Next to the process of the invention, the present invention also provides a chemical plant suitable for the production of purified epsilon-caprolactam from Nylon 6-containing multi-component material that comprises at least (A) a Nylon 6-pre-concentration section, (B) a depolymerization section, (C) a recovery section, and (D) a purification section, wherein the plant, and in particular said four sections, are configured for carrying out the process of the invention.

The present invention also provides purified epsilon-caprolactam that is obtainable by the process of the invention and has a product carbon foot print of less than 2.5 kg $CO_2$ equivalent per kg purified epsilon-caprolactam (based on data originating from ecoinvent version 3.7.1; location: Europe). Finally, the invention provides the use of epsilon-caprolactam recovered from Nylon 6-containing multi-component material for reducing the carbon footprint of an epsilon-caprolactam production plant that at least also produces epsilon-caprolactam from a Beckmann rearrangement of cyclohexanone oxime. Advantageous embodiments of the invention are indicated in the dependent claims and are explained in more detail in the following.

DETAILED DESCRIPTION OF THE INVENTION

The Nylon 6-Containing Multi-Component Material

The process of the invention uses Nylon 6-containing multi-component materials as starting material. The Nylon 6-containing multi-component material typically is a solid, in particular a solid body, net, sheet or film material.

Multi-component materials comprise two or more components. They are often used as a means of combining the properties of different components into a single material. The term "component" as used herein refers to a chemical substance. In a preferred embodiment, the Nylon 6-containing multi-component material comprises Nylon 6 and at least one non-Nylon 6 polymer as components. The two or more components can be present as separate domains in the multi-component material (e.g., in a sheath and core configuration, an islands-in-the-sea configuration, a side-by-side configuration, multi-layer configuration or other configurations). Alternatively or additionally, the multi-component material can comprise a mixture of different components (e.g., in the form of polymer blends). Also mixtures of these two embodiments are possible, e.g., in the case of a multi-layer film comprising a layer of a single polymer and an additional layer of a polymer blend or polymer matrix filled with polymer filler particles. Typically, the Nylon 6 is present in the Nylon 6-containing multi-component material as a separate domain and/or as a mixture with the at least one non-Nylon 6 polymer.

Preferably, the components of the multi-component material are at least two different polymers, one of which is or comprises Nylon 6. In one embodiment at least two components of the multi-component material comprise or consist of polymers. In this embodiment, the multi-component materials can comprise further non-polymer components. However, preferably, more than 80 wt. % of the multi-component material is made up of polymers. The term "polymer" used herein refers to the terms usual meaning, i.e., a large molecule (e.g. oligomer) or macromolecule composed of repeating subunits. Polymers, as used herein, can be of synthetic origin such as plastics including polypropylene, Nylon 6 and polystyrene or of natural origin such as starch or proteins. The term "polymer" as used herein also includes homopolymers, copolymers and polymer blends. Polymers of natural and synthetic origin are created via polymerization of many small molecules, known as monomers. Homopolymers are prepared from only one type of monomer. Copolymers are prepared from different types of monomers, which can be in random or block configuration. "Polymer blend" or "blend" as used herein means a composition of two or more polymers and are usually obtained by extrusion. The blend may or may not be miscible, it may or may not be phase separated.

In one embodiment, at least one component of the multi-component material comprises or consists of Nylon 6 and the at least one other component of the multi-component material comprises or consists of a polymer that is different from Nylon 6. The polymer different from Nylon 6 can be selected from the group consisting of polyolefins (especially polyethylenes and polypropylenes), polyethylene oxide, polypropylene oxide, polycaprolactone, polyamides (other than polyamide 6), polyesters, polyvinylidene fluoride, polyvinylidene chloride, polystyrene, polycarbonate, polymethylmethacrylate, ethylene-co-acrylic acid copolymers, polyoxymethylene, ethylene vinyl alcohol, polyurethanes and a combination, in particular blend, thereof. Particularly good results in terms of obtained epsilon-caprolactam purity and yield can be achieved when the polymer different from Nylon 6 is selected from the group consisting of polyolefins (especially polyethylenes and polypropylenes), polyamides (other than polyamide 6, in particular polyamide 6,6, polyamide 4,6, polyamide 6,10, polyamide 12) and a combination thereof.

The multi-component material employed in the process of the invention comprises Nylon 6. The term "Nylon 6" used herein refers to polycaprolactam. The term "Nylon 6-containing multi-component material" used herein refers to a multi-component material that comprises two or more components of which one is or comprises Nylon 6. The weight fraction of Nylon 6 in the Nylon 6-containing multi-component material which is used in the process of the invention is not critical to practice the invention and can range from 0.5 wt. % to 99 wt. %. It is a special advantage of the process of the invention, however, that it works so well also for multi-component materials containing only lower contents of Nylon 6 as compared to the greater than 80 wt. % content of Nylon 6 that are required for the processes of the prior art to successfully be applied in practice. Therefore, according to a particular advantageous embodiment, the weight fraction of Nylon 6 in the Nylon 6-containing multi-component material used in the process of the invention is from 1 wt. % to 75 wt. %, more preferably from 1 wt. % to 60 wt. %, even more preferably from 2 wt. % to 35 wt. % and most preferably from 3 wt. % to 25 wt. %. If not otherwise indicated, all wt. % values stated herein are always based on the total weight of the Nylon 6-containing multi-component material.

The Nylon 6-containing multi-component material might have any shape, including (multi-filament) yarn, chip, film or any moulded form. The shape of the Nylon 6-containing multi-component material used for the process of the invention is not critical.

Preferably, the Nylon 6-containing multi-component material used in the process of the invention is a multi-layer material, wherein at least one layer comprises or consists of Nylon-6. The term "multi-layer material" used herein refers to material which is organized in different layers. The layers can differ in their relative position, thickness and/or composition. The layers can be of the same or of different type. Preferably, the multi-layer material contains at least one layer that does not comprise Nylon 6. In a further preferred embodiment the multi-layer material comprises two skin layers as outermost layers on opposite sides of the multi-layer material, wherein both skin layers do not comprise Nylon 6, which is thus contained in one of the layers sandwiched in between the skin layers. Nonlimiting examples of suitable polymers that can be used in the skin layers include polypropylenes, polyethylenes, polyethylene oxide, polycaprolactone, polyamides (other than Nylon 6), polyesters, polyvinylidene fluoride, polyvinylidene chloride, polystyrene, polycarbonate, ethylene vinyl alcohol, polymethylmethacrylate, ethylene-co-acrylic acid copolymers, polyoxymethylene and blends of two or more of these. A particular advantage of the process of the invention is that it works with multi-layer materials in which the Nylon 6 does not need to be exposed or accessible at the surface of the material.

As non-Nylon 6-containing skin or intermediate layer, the multi-layer material can contain a barrier layer. The barrier layer may be formed from any material with barrier properties. The barrier layer may comprise or consist of organic material, e.g., carbon; inorganic material, e.g., metal, ceramic, oxide; polymer material or a combination thereof. Nonlimiting examples of suitable polymers other than Nylon 6 that can be employed in or as the barrier layer include: polyethylene terephthalate, ethylene vinyl alcohol, polyvinylidene chloride copolymers, polyamides (not being Nylon 6), polyketones, blends of two or more of these; and blends with other polymers comprising one or more of these.

The multi-layer material may comprise tie or adhesive layers connecting the at least one Nylon 6-containing layer with the other layer(s) in the multi-layer material. Nonlimiting examples of suitable polymers that can be employed as tie or adhesive layers include: olefin block copolymers such as propylene-based block copolymer sold under the tradename INTUNE™ (The Dow Chemical Company) and ethylene-based block copolymer sold under the tradename INFUSE™ (The Dow Chemical Company); polar ethylene copolymers such as copolymers with vinyl acetate, acrylic acid, methyl acrylate, and ethyl acrylate; ionomers; maleic anhydride-grafted ethylene polymers and copolymers; polyurethane adhesives; blends of two or more of these; and blends with other polymers comprising one or more of these.

In a preferred embodiment, "layer" as used herein refers to a "film". Even more preferably, the Nylon 6-containing multi-component material used in the process of the invention is itself a film, i.e., a multi-layer film that contains at least one layer that comprises or consists of Nylon 6. Preferably, the multi-layer film contains at least one layer comprising or consisting of Nylon 6 and at least one layer not comprising Nylon 6. The multi-layer film can be produced by any film lamination and/or coextrusion technique. The term "film" as used herein is defined as being a thin sheet with a thickness of less than 1 mm. "Layers" in films can be very thin, as in the cases of nanolayers. "Film" as used herein can be in the form of shapes, such as profiles, parisons, tubes, and the like, that are not necessarily "flat" in the sense of planar. In a preferred embodiment, the term "film" as used herein means a film consisting of or comprising more than 80 wt. % of polymer material. The use of multi-layer films in the process of the invention is advantageous since it is a common waste product. The majority of today's packaging films are multi-layer films. According to a practically particularly relevant embodiment, the "multi-layer film" as used herein is a packaging film, in particular a modified atmosphere packaging film, both of which are described in the background section above.

Due to the intimate connection between the film layers, it was very difficult prior to this invention to recover high-grade epsilon-caprolactam from Nylon 6-containing multi-layer films, especially if the Nylon 6-content was below 80 wt. % as indicated above and/or if the at least one Nylon 6-containing layer is sandwiched in between two non-Nylon 6-containing layers, which can but need not be skin layers, in the multi-layer film and therefore not very accessible. These types of multi-layer films, when used as Nylon 6-containing multi-component materials in step a), therefore present particularly advantageous embodiments of the invention. Thus, in particular, the Nylon 6-containing multi-component material used in the process of the invention can be a multi-layer film that contains at least one layer comprising or consisting of Nylon 6 that is sandwiched (i.e., embedded in between) in between two or more layers not comprising Nylon 6. The multi-layer film may of course comprise further layers with or without Nylon 6 at any position in between, on top or below these layers.

The process of the invention has the advantage that unlike processes of the prior art that were, e.g., restricted to Nylon 6-containing fibers derived from carpets that needed to be subjected to a mechanical pre-processing step, the process of the invention is not so limited and in particular can also be applied very successfully to multi-layer films. In a particular embodiment, the Nylon 6-containing multi-component material used in the process of the invention is not a carpet or a material derived from carpet. In another embodiment it is not a textile or material derived from a textile. In another embodiment it does not comprise Nylon 6 fibres.

Possible Pre-Treatment Steps

The material derived from Nylon 6-containing multi-component material that is used in step a) has been obtained by extracting a Nylon 6-containing multi-component material with one or more solvents to obtain a solid pre-concentrated Nylon 6-containing material, which is enriched in Nylon 6 as compared to the Nylon 6-containing multi-component material. This is described in more detail below. Before or after this pre-treatment, the material can be advantageously subjected to further pretreatment steps, which are described in the following.

Before being subjected to process step a) of the invention, the Nylon 6-containing multi-component material preferably undergoes a pre-treatment, in particular a mechanical size reduction and/or washing step. Thus, a mechanical size reduction and/or washing section can precede the Nylon 6-pre-concentration section in the process of the invention. Preferably, the Nylon 6-containing multi-component material is fragmented into pieces before it is extracted with one or more organic solvents in the Nylon 6-pre-concentration section in step a). This mechanical pre-treatment, i.e., the mechanical comminution or fragmentation of the Nylon 6-containing multi-component material, can be achieved, e.g., by cutting, shredding, milling, grinding, chipping. In a preferred embodiment, the Nylon 6-containing multi-component material is charged to step a) in the form of pieces which have on average, along the longest axis of the piece, a length of 0.01 to 100 cm, preferably from 0.05 to 10 cm and most preferably from 0.1 to 5 cm. The skilled person can easily determine the average length along the longest axis of the employed pieces by first taking a representative sample of the pieces, then measuring the length of the longest axis of each of these pieces (e.g., 50 pieces), and finally calculating the average value of all these individual measurements. The preferred particle dimensions can also be described in terms of average particle weight. Preferably, the pieces of Nylon 6-containing multi-component material have an average particle weight from 0.1 milligram to 100 kilogram, preferably from 1 milligram to 10 kilogram, more preferably from 10 milligram to 1 kilogram and most preferably from 10 milligram to 100 gram. Using pieces of Nylon 6-containing multi-component material with the aforementioned dimensions has the advantage that the surface area is increased and/or the pieces can be more easily handled and/or mixed with the organic solvent which is added for the extraction in the Nylon 6-pre-concentration section.

Optionally, the Nylon 6-containing multi-component material is cleaned prior to being Nylon 6-pre-concentrated. This is advantageous because any (adhering) dirt that is removed will consequently not perturb the next steps of the process of the invention.

As used herein, the term "cleaning" is defined as any process of removing non-Nylon 6 materials that are adhered to Nylon 6-containing multi-component material or that are mixed with Nylon 6-containing multi-component material. Cleaning is advantageous because any non-Nylon 6 material that is removed will consequently not perturb the next steps of the process of the invention.

Optionally, the Nylon 6-containing multi-component material is cleaned by washing with a solvent, preferably water, prior to being charged to the Nylon 6-pre-concentration section. This is advantageous because any (adhering) dirt is removed which consequently does not perturb the next steps of the process of the invention. Preferably, washing agents ranging in concentrations from 0 to 30% by weight relative to the solvent are added to the solvent for an improved washing efficiency. In another preferred embodiment, the washing process includes a final rinsing step with (clean) washing solvent without washing agent in order to remove residues of washing agent and dirt present that are adhering to the Nylon 6-containing multi-component material. Preferably, the washing solvent is heated to further enhance the washing process. Optionally, the Nylon 6-containing multi-component material is dried after the cleaning step and prior to being charged to the Nylon 6-pre-concentration section. This has the advantage that the solvent which is added for the extraction therein is not diluted by or contaminated with the washing solvent. The washing is preferably carried out under friction. Different types of industrial washing systems are available on the market, like rotary plastic washers and (high speed) friction washers. Optionally, the mechanical size reduction and washing of the Nylon 6-containing multi-component material are combined in e.g., so-called wet crushing machines.

Optionally, prior to the mechanical comminution or fragmentation of the Nylon 6-containing multi-component material, metal fragments, rocks and other disturbing materials that cause severe wear of the equipment used for the mechanical comminution or fragmentation are removed. Preferably, non-Nylon 6 comprising materials, like polyethylene, polypropylene and Nylon 6,6 comprising materials are removed prior to the mechanical comminution or fragmentation of the Nylon 6-containing multi-component material or afterwards as described further below. The removal of foreign materials can be done mechanically or manually. The removal of these disturbing materials has the advantage that the maintenance costs of the equipment used for the mechanical comminution or fragmentation can be reduced to a large extent. In addition, the Nylon 6 content of the material obtained after mechanical comminution or fragmentation is higher than without removal of the disturbing materials. Optionally, foreign materials are separated from the Nylon 6-containing multi-component material that have been mechanically comminuted or fragmented. To this end, various separation processes can be applied, including, but not limited to, density separation and magnetic separation. In density separation, materials of different densities are placed in a liquid of intermediate density, where the less dense material floats and separates out from the more dense sinking material. In practice, density separation is often done by a series of density separation stages. E.g., in one stage, the high density materials like rocks, sand and metals (including iron and lead) are separated off, while in another stage low density materials, like polyolefins polypropylene and polyethylene, are separated off. Magnetic separation is the process of separating components of mixtures by using magnets to attract magnetic materials. The process that is typically used for magnetic separation detaches magnetic material from non-magnetic material. The removal of foreign materials in the comminuted or fragmented Nylon 6-containing multi-component material is advantageous because such materials can disturb the subsequent steps of the process of the invention. Optionally, Nylon 6-containing multi-component material, that is preferably washed and reduced in size, is densified. Preferably, densification of Nylon 6-containing multi-component material is done by charging to a smelter (e.g., an extruder) or by compacting in a (mechanical) compactor or in a agglomerator. Densification of Nylon 6-containing multi-component material that is preferably cleaned and/or reduced in size has the advantage of an increased bulk density, which reduces the costs of intermediate storage and transportation in case the pretreatment is done at a different location (see below).

In the smelter the Nylon 6-containing multi-component material is melted. Preferably, the resulting polymer melt is filtered. This has the advantage that solid impurities are removed. The melted and optionally filtered polymer melt is then cooled and preferably fed to a pelletizer. The pelletizer cuts the product into pellets. The dimensions and the shape of the pellets (also often called granules) can be chosen within wide limits. In general, pellets are cylindrical in shape (originating from thin strands that are chopped into pieces). Other shapes like (non-perfect) spheres, however, are also possible. The dimensions of the pellets can be chosen within wide limits. Usually, pellets have a diameter that ranges from 1 to 10 mm, preferably from 2 to 7 mm, more preferably from 3 to 5 mm. In a preferred embodiment, pellets have a length that ranges from 1 to 50 mm, preferably from 2 to 25 mm, more preferably from 3 to 15 mm.

Pelletization of Nylon 6-containing multi-component material that is preferably cleaned and reduced in size has the advantage of an increased bulk density, which reduces the costs of intermediate storage and transportation in case the pretreatment is done at a different location (see below). Apart from density increase, pelletization also offers other benefits, such as a homogeneous shape and structure of the to-be-treated material which is advantageous for (automated) feeding into equipment applied for Nylon 6-pre-concentration by extraction with a solvent.

The site where the pre-treatment of the Nylon 6-containing multi-component material is performed and the site where the Nylon 6-pre-concentration by extraction with a solvent is located can be the same. However, preferably, one or more of the pre-treatment steps are done at different locations, e.g., at a location that is specialized in pre-treatment of wasted polymer materials and especially Nylon 6-containing multi-component material. Nylon 6-containing multi-component materials that have been pre-treated at various locations can then be shipped to the site where the Nylon 6-pre-concentration by extraction with a solvent is located.

Therefore, according to a particular advantageous embodiment of the invention, prior to step a) matter comprising Nylon 6-containing multi-component material is subjected to a pre-treatment and pre-concentration to obtain material derived from Nylon 6-containing multi-component material in a pre-treatment section [A], in particular a cleaning in cleaning section and/or mechanical size reduction in a mechanical size reduction section and/or a densification section and an extraction section.

The Nylon 6-Pre-Concentration Step a)

In step a) of the process of the invention, the Nylon 6-containing multi-component material is extracted in the Nylon 6-pre-concentration section with one or more organic solvents to obtain a solid pre-concentrated Nylon 6-containing material, which is enriched in Nylon 6 as compared to the Nylon 6-containing multi-component material. This is an important step of the process of the invention, ensuring high yields and the high quality of epsilon-caprolactam that can be obtained with the invention. This step is particularly important when multi-layer films are used as starting material, in particular when the Nylon 6-containing layer is sandwiched in between other polymer layers and therefore not directly accessible for depolymerization. The pre-concentration of Nylon 6-containing multi-component material is also particularly important when multi-component material comprising Nylon 6 and at least one non-Nylon 6 polymer are used as starting material, in particular when the Nylon 6 is present in the Nylon 6-containing multi-component material as a separate domain and/or as a mixture with the at least one non-Nylon 6 polymer and therefore not directly accessible for depolymerization.

The extraction in the Nylon 6-pre-concentration section according to the invention typically comprises the following steps:

(i) adding the one or more organic solvents to the Nylon 6-containing multi-component material;

(ii) performing a phase separation to obtain a liquid extract phase comprising solvent and dissolved components from the Nylon 6-containing multi-component material and an at least partially solid phase comprising undissolved components of the Nylon 6-containing multi-component material and optionally solvent;

(iii) removing the solvent from the liquid extract phase and, if present therein, also from the at least partially solid phase to obtain two solid phases, one of which is the pre-concentrated Nylon 6-containing material that is enriched in Nylon 6 as compared to the Nylon 6-containing multi-component material that is used as starting material.

Step (i) of course also includes a treatment with the solvent, i.e., the solvent and the Nylon 6-containing multi-component material are contacted for a sufficient time and under conditions sufficient to allow for dissolving of components from the Nylon 6-containing multi-component material that are to be extracted. The phase separation in step (ii) can be performed by any suitable means known for solid/liquid phase separation. Suitable phase-separation means are, e.g., filters, centrifuges, cyclones. The solvent removal in step (iii) is advantageously performed by evaporation of the solvent, whereby the dissolved components that were extracted from the Nylon 6-containing multi-component material are obtained as remaining solid precipitate.

However, various technologies exist and can be used which enable the recovery of a solvent from the dissolved compounds. These technologies are known to the skilled person and include cooling down, evaporation, distillation, precipitation by addition of a precipitation agent (solvents for depositing the dissolved polymers) and combinations thereof.

The term "extraction", "extracted", or "extracting", as used herein, means a physical or chemical method of removing one or more components from a substrate by means of a solvent followed by solvent removal and recovery of the extracted component(s). The one or more solvents can be used in the process of the invention to extract either Nylon 6, in which case the pre-concentrated Nylon 6-containing material is obtained as remaining solid residue after removal of the one or more solvents from the liquid solvent-containing extract phase, and/or to extract non-Nylon 6-compounds from the Nylon 6-containing multi-component material, in which case the remaining undissolved Nylon 6-containing multi-component material, optionally after removal of any adhering solvent, is the pre-concentrated Nylon 6-containing material referred to herein.

The term "pre-concentrated" used herein refers to the extraction of a Nylon 6-containing multi-component material with one or more solvents with subsequent solvent removal to obtain a material that is enriched in Nylon 6, as compared to the Nylon 6-containing multi-component material that is used as starting material. "Enriched in Nylon 6" means enriched as compared to the Nylon 6 comprising multi-component material that is used as starting material. The enrichment in Nylon 6, is defined as the content of Nylon 6 in wt. %, based on the total weight of polymers in the solid Nylon 6-containing material obtained after extraction compared to the content of Nylon 6 in wt. %, based on the total weight of polymers in the Nylon 6 comprising multi-component material that is used as starting material. This enrichment is very much dependent on the fraction of non-Nylon 6 compounds that is removed. The degree of enrichment in the pre-concentrated Nylon 6-containing material is advantageously of from 1.1 to 50, in particular of from 1.2 to 30, and more particularly of from 1.5 to 10. In case the starting material had a Nylon 6 content of 20 wt. %, based on the total polymer content, and the pre-treated Nylon 6 containing phase has a Nylon 6 content of 80 wt. %, based on the total polymer content, then the degree of enrichment in Nylon 6 is (80 wt. % divided by 20 wt. %=) 4.

The solvents used for the extraction in the Nylon 6-pre-concentration section can be organic or inorganic solvents. Preferably, the solvent is an organic solvent. The extraction of the Nylon 6-containing multi-component material with an organic solvent has the advantage that different components, in particular different polymers can be separated from each other, and in particular from the Nylon 6 that is to be enriched, by their different solubilities in certain solvents.

The extraction usually involves (i) contacting the Nylon 6-containing multi-component material with one or more solvents so that a liquid extract phase comprising solvent and dissolved compounds from the Nylon 6-containing multi-component material and a usually solid or partially solid second phase consisting of the undissolved Nylon 6-containing multi-component material is obtained, followed by (ii) a phase separation and (iii) solvent removal to obtain a pre-concentrated Nylon 6-containing material.

As explained above, depending on whether (1) a Nylon 6- or (2) a non-Nylon 6-dissolving solvent is used, the pre-concentrated Nylon 6-containing material is obtained (1) after solvent removal from the liquid extract phase comprising dissolved Nylon 6 or (2) from the solid or partially solid second phase consisting of the undissolved, remaining Nylon 6-containing multi-component material. Two or more different, in particular complementary, extractions can also be combined.

In the case of more than one solvent, the treatment can occur simultaneously or sequentially. If more than one solvent is used, the solvents should be distinguished in their ability to dissolve Nylon 6. In a particular advantageous embodiment of the invention, step a) comprises an at least two-step procedure, in which (i) the Nylon 6-containing multi-component material is first extracted with a solvent that is able to dissolve non-Nylon 6-components, and subsequently, (ii), the undissolved, remaining Nylon 6-containing multi-component material from that first extraction is treated and extracted with a solvent that is able to dissolve Nylon 6, whereby after phase separation the pre-concentrated Nylon 6-containing material is obtained, after removal of the solvent from the liquid extract phase comprising dissolved Nylon 6 that is obtained from that second extraction. Proceeding in this way is particularly advantageous when multi-layer films are used as starting material, in particular when the Nylon 6-containing layer is covered, in particular sandwiched in between other polymer layers, and therefore not directly accessible to Nylon 6-dissolving solvents.

By the choice of the solvent(s) and the treatment conditions (e.g., temperature, treatment length and amount of solvent relative to the amount of Nylon 6-containing multi-component material), the effect of the extraction can be influenced. Depending on the solvent(s) used, the extraction in step a) can be of the following type:

Pre-concentration steps, in which non-Nylon 6 compounds are preferentially extracted from the Nylon 6-containing multi-component material (then the obtained pre-concentrated Nylon 6-containing material is the non-extracted Nylon 6-containing multi-component material, optionally after removal of any adhering solvent);

Pre-concentration steps, in which Nylon 6 compounds are preferentially extracted from the Nylon 6-containing multi-component material (then the pre-concentrated Nylon 6-containing material is obtained after removal of the solvent from the liquid extract phase comprising solvent and dissolved Nylon 6); and Nylon 6 and non-Nylon 6 compounds are preferentially extracted from the Nylon 6-containing multi-component material in a sequential manner, i.e., a combination of extractions for non-Nylon 6 compounds and Nylon 6 is performed sequentially.

Extractions, in which non-Nylon 6 compounds are preferentially extracted from the Nylon 6-containing multi-component material can be performed with solvents that are suitable as selective extraction agents for non-Nylon 6 compounds. These are solvents in which non-Nylon 6 compounds are readily dissolved, while dissolution of Nylon 6 in the solvent is limited. These solvents must have a high selectivity towards the dissolution of non-Nylon 6 compounds. Apart from the choice of the solvent, also the temperature at which the extraction is performed, the treatment time and amount of solvent relative to the amount of Nylon 6-containing multi-component material can have a major impact on the extraction selectivity. The choice of these parameters therefore depends on the type of non-Nylon 6-containing components that shall be selectively removed. The skilled person can easily determine via simple test dissolution experiments, which solvents work for extracting the relevant non-Nylon 6-containing components in a given Nylon 6-containing multi-component material.

Any one or more of the organic solvents mentioned below in respect of particular non-Nylon 6 compounds can be used as a solvent in the process of the invention.

For dissolving polyolefines (e.g., LD, LLD and HD polyethylene and polypropylene), e.g., solvents selected from the group consisting of aliphatic hydrocarbons, naphthenic hydrocarbons, aromatic hydrocarbons and mixtures thereof are particularly useful. They are obtained as boiling fractions in petroleum processing for the production of fuels like petrol and diesel. The aforementioned boiling fractions include paraffin wax, petroleum wax and white spirit, each of which can be used as solvent according to the invention. Isomeric mixtures of xylenes or pure solvents like toluene are also known to dissolve polyolefines. Chlorinated hydrocarbons like tetrachloroethane can also be used to dissolve polyolefins.

For dissolving polystyrenic polymers, a wide variety of solvents including aromatic organic solvents may be used. Preferably, benzene, toluene, xylene and mixtures thereof are used as solvents to dissolve polystyrenic polymers. Most preferably, xylene is used to dissolve polystyrenic polymers.

For dissolving polyvinyl chlorides, the solvents tetrahydrofuran, cyclohexane, dioxane and methylethylketone (MEK) and mixtures thereof are used preferably.

Solvents that can be used to dissolve other (polymeric) non-Nylon 6 compounds are known to the skilled person or can easily be identified by performing test dissolution experiments. When choosing the solvent(s) for the extraction in the Nylon 6-pre-concentration section, the flexibility of the process of the invention allows to take other factors into account including inter alia the stable commercial availability, the ease of handling, health aspects and the cost of the solvent.

After an extraction in which non-Nylon 6 compounds are preferably extracted with a solvent, the non-dissolved compounds are removed by phase separation from the mixture obtained in the Nylon 6-pre-concentration section. The extraction should be performed in a way that the largest proportion by weight of the non-dissolved compounds upon extraction with a solvent that preferentially dissolves non-Nylon 6 compounds should be Nylon 6. The non-dissolved material, optionally, after removal of any adhering solvent, then represents the pre-concentrated Nylon 6-containing material, which is enriched in Nylon 6. The employed solvent is usually recovered from the extract phase and re-used in the Nylon 6-pre-concentration section.

Optionally, the extraction, in which non-Nylon 6 compounds are preferentially extracted, is performed more than once. By selecting another solvent and/or other process conditions (e.g., another extraction temperature), non-Nylon 6 compounds that were not removed in a previous extraction can be removed in the additional extraction. After every extraction, a pre-treated, usually solid or partially solid, Nylon 6-containing phase is obtained, which is more enriched in Nylon 6 than the pre-concentrated Nylon 6-containing material resulting from the previous extraction. In each extraction, more and more non-Nylon 6 compounds are gradually extracted from the Nylon 6 comprising multi-component material.

Alternatively or as a complementary extraction to the extractions with non-Nylon 6-dissolving solvents described above, extractions, in which Nylon 6 is preferentially extracted from the Nylon 6-containing multi-component material, can be performed with solvents that are suitable as selective extraction agents for Nylon 6. To preferentially extract Nylon 6, solvents are used that dissolve Nylon 6, while dissolution of non-Nylon 6 is limited in these solvents. In other words, solvents with a high selectivity towards dissolution of Nylon 6 should be used. Like for the selective dissolution of non-Nylon 6 compounds, also the selective dissolution of Nylon 6 compounds can be influenced by the choice of the solvent, the temperature at which the extraction is performed, the treatment time and amount of solvent relative to the amount of Nylon 6-containing multi-component material.

Solvents known from prior art processes for extracting polyamides can be used in this Nylon 6-specific extraction step. For example, EP603434 discloses suitable solvents for the dissolution of polyamides including Nylon 6. The solvents include concentrated inorganic acids, formic acid, chloroacetic acid, phenols, cresols, alcoholic solutions of alkaline earth halides, aromatic alcohols such as phenylethanol and benzyl alcohol, as well as glycols, lactams and lactones. U.S. Pat. No. 5,840,773 discloses as solvents for dissolving polyamides such as Nylon 6 aliphatic alcohols, e.g., methanol, ethanol, n-propanol, isopropanol, n-butanol, isobutanol, tert-butanol, pentanol, hexanol, 2-ethylbutanol, 4-methylpentanol, 1-heptanol, 2-heptanol, 4-heptanol, 2,4-dimethylpentanol, 1-octanol, 2-octanol, 2-ethylhexanol, 1-nonanol, 2-nonanol, n-decanol, n-undecanol, n-dodecanol, n-tridecanol, n-tetradecanol, n-pentadecanol, n-hexadecanol, n-octadecanol, and the like, and substituted monohydric and dihydric alcohols, such as 2-methoxy-1-ethanol and methylene glycol. In a preferred embodiment of U.S. Pat. No. 5,840,773, $C_1$-$C_{12}$ alcohols are employed. In particular, methanol and ethanol are preferably employed as extraction agent. The extraction agent might be a mixture of an aliphatic alcohol and water. U.S. Pat. No. 5,840,773 further discloses that an extraction time of 60 minutes has been found to be suitable for a methanol extraction of polyamide-6, with the extraction preferably being carried out in an autoclave at a temperature of about 135-° C. to about 140° C. Along these lines, U.S. Pat. No. 5,840,773 mentions that polyamide-6,6 is preferentially dissolved in methanol at a temperature of at least about 140° C. In Example IV of U.S. Pat. No. 5,840,773 an extraction temperature for polyamide-6,6 of about 160° C. is applied.

Optionally, the extraction, in which Nylon 6 is preferentially extracted, is performed more than once. After every extraction, a pre-concentrated Nylon 6-containing material is obtained, which is more enriched in Nylon 6 than the pre-concentrated Nylon 6-containing material resulting from the previous extraction. This seems to be due to the fact that the amount of impurities in the pre-concentrated Nylon 6-containing material which typically comprises non-Nylon 6 compounds is gradually reduced by each extraction.

After an extraction in which Nylon 6 compounds are preferentially extracted with a solvent, the solvent is recovered. In doing so, firstly, non-dissolved material is removed, e.g., by filtration or centrifugation, from the liquid extract phase that contains solvent and Nylon 6. The extraction should be performed in a way that the largest proportion by weight of the non-dissolved compounds are non-Nylon 6 compounds. Secondly, solvent is recovered from the Nylon 6-containing liquid extract phase to obtain the pre-concentrated solid Nylon 6-containing material, which is enriched in Nylon 6. Any of the above-described solvent removal technologies can be performed to separate dissolved Nylon 6-containing material from the solvent, including cooling down, evaporation, distillation, precipitation by addition of a precipitation agent (solvents for depositing the dissolved polymers) and combinations thereof.

Extractions can also be combinations of sequential extractions with solvents that preferentially extract non-Nylon 6 compounds and solvents that preferentially extract Nylon 6. By such a combination of sequential extractions a Nylon 6-containing phase is obtained that is even more enriched in Nylon 6 than a Nylon 6-containing phase pre-treated only once.

In an embodiment of the invention, the Nylon 6-containing multi-component material is first extracted in a first Nylon 6-pre-concentration section with a solvent that preferentially extracts non-Nylon 6 compounds from the Nylon 6-containing multi-component material to obtain a pre-concentrated Nylon 6-containing material, which is enriched in Nylon 6. In a second extraction, the pre-concentrated Nylon 6-containing material, which is enriched in Nylon 6 is treated with a solvent that preferentially extracts Nylon 6 compounds from the pre-concentrated Nylon 6-containing material, which is enriched in Nylon 6 to obtain a pre-concentrated Nylon 6-containing material, which is further enriched in Nylon 6. This can then be used in step b). For example, in a first extraction, the non-Nylon 6 compound LD polyethylene is removed from the Nylon 6-containing multi-component material by extraction with white spirit. In a second extraction, the pre-concentrated Nylon 6-containing material, which is enriched in Nylon 6 is further extracted with methanol or aqueous methanol (e.g., weight ratio water to MeOH 1:19), whereby an even further pre-concentrated solid Nylon 6-containing material is obtained after removal of the solvent (methanol, water).

According to another advantageous embodiment of the invention, the Nylon 6-containing multi-component material is first treated in a first Nylon 6-pre-concentration section with a solvent that preferentially extracts Nylon 6 compounds from the Nylon 6-containing multi-component material to obtain the pre-concentrated Nylon 6-containing material, which is enriched in Nylon 6. In a second extraction, the pre-concentrated Nylon 6-containing material, which is enriched in Nylon 6, is treated with a solvent that preferentially extracts non-Nylon 6 compounds from the pre-concentrated Nylon 6-containing material, which is enriched in Nylon 6 to obtain a pre-concentrated Nylon 6-containing material, which is further enriched in Nylon 6. For example, in a first extraction Nylon 6 is extracted from the Nylon 6-containing multi-component material with ethanol to form, after recovery of the ethanol, the Nylon 6-containing phase which is enriched in Nylon 6. In a second extraction, the pre-concentrated Nylon 6-containing material, which is enriched in Nylon 6 from which non-Nylon 6 components are further extracted with toluene, whereby a Nylon 6-containing phase is obtained which is further enriched in Nylon 6.

The extraction with the solvent in the Nylon 6-pre-concentration section is performed at temperatures between 0° C. and 350° C. (at higher temperatures, Nylon 6 decomposes), more preferably between 20° C. and 210° C. and most preferably between 50° C. and 190° C. In this temperature range, the selective extraction of most solvents is enhanced.

The time needed for the extraction in the extraction section, i.e., the extraction with the solvent, can be easily determined by the skilled person via routine experimentation. The time allowed for extraction should preferably take into account the type of Nylon 6-containing multi-component material and the amount of Nylon 6 comprised therein and the accessibility thereof. The time needed for extraction can range from seconds to hours. Preferably, the time needed for extraction is more than 5 seconds and less than 6 hours. More preferably, the time needed for extraction is more than 15 seconds and less than 2 hours.

As a consequence of the extraction in the Nylon 6-pre-concentration section, a solid pre-concentrated Nylon 6-containing material is obtained that is enriched in Nylon 6. The term "solid" in this respect refers to the state of the material at room temperature (20° C.). At higher temperatures, the pre-concentrated Nylon 6-containing material can also be present as a melt. The pre-concentrated Nylon 6-containing material is stable and can be stored for future use in step b) of the process of the invention or transported to a depolymerization section at a different location for this purpose. Thus, similarly as explained for the other pre-treatment steps above, the site where the Nylon 6-pre-concentration by extraction with a solvent and the location(s) where steps a) to d) of the method of the invention are performed can be the same or different. Preferably, one or more of the pre-treatment and pre-concentration steps are done at different locations, e.g., at a location that is specialized in pre-treatment of wasted polymer materials and especially Nylon 6-containing multi-component material. Nylon 6-containing multi-component materials that are pre-treated and have been pre-concentrated at various locations can then be shipped to the site where one or more of steps a) to d) of the method of the invention are performed.

The Depolymerization Step b)

In step b) of the invention, the pre-concentrated Nylon 6-containing material, which is enriched in Nylon 6 and obtained in the Nylon 6-pre-concentration section, is charged to the depolymerization section and is depolymerized to form epsilon-caprolactam. The formed epsilon-caprolactam is discharged from the depolymerization section as an epsilon-caprolactam comprising stream. The depolymerization section comprises one or more depolymerization reactors that are operated in series and/or in parallel.

Optionally, the pre-concentrated Nylon 6-containing material is mechanically compressed into a smaller volume prior to being charged to the depolymerization section. In particular, the pre-concentrated Nylon 6-containing material can be compressed into particles with an increased density prior to being charged to the depolymerization section, e.g., by mechanical compaction or by extrusion of melted material followed by cooling and cutting it to size or by forming of droplets of melted material that are thereafter solidified by cooling. Such compression has the advantage that less volume is needed for intermediate storage and transport and might facilitate dosing to the depolymerization section.

Optionally, the pre-concentrated Nylon 6-containing material is dried before being charged to the depolymerization section. This has the advantage that less or no solvent is introduced to the depolymerization section. Solvent introduced in the depolymerization section might negatively influence the depolymerization process (e.g., reduced depolymerization reaction rates, higher consumption of catalyst, the vapor stream comprising epsilon-caprolactam and water that is obtained in the depolymerization section might contain more impurities).

The pre-concentrated Nylon 6-containing material is preferably fed to the depolymerization reactor(s) as a solid phase or as a melt. Feeding as a melt may be achieved by using an extruder, gear pump, or other means known by the skilled person.

The feeding of the pre-concentrated Nylon 6-containing material to the depolymerization reactor(s) may be realized by continuous or by intermittent dosing of the pre-concentrated Nylon 6-containing material which is enriched in Nylon 6.

In the depolymerization section, the pre-concentrated Nylon 6-containing material is depolymerized to form epsilon-caprolactam. This is achieved by contacting the pre-concentrated Nylon 6-containing material with water, which preferably is in the form of steam. Feeding the water as steam to the depolymerization reactor allows, optionally without further heating, to obtain the vapor stream comprising epsilon-caprolactam and water that is required as a product of step b) according to the invention. The also required weight to weight ratio of 2:1 to 15:1 of water to epsilon-caprolactam in this vapor stream can be obtained by adjusting the ratio of steam to pre-concentrated Nylon 6-containing material that is fed into the depolymerization section. During the depolymerization reaction, decomposition products may be formed including linear oligomers of epsilon-caprolactam and cyclic oligomers of epsilon-caprolactam. In addition, the feed stream of the pre-concentrated Nylon 6-containing material, which is enriched in Nylon 6, may also contain other components, i.e., impurities such as non-Nylon 6 compounds and residues of solvents(s) applied in the Nylon 6-pre-concentration section, that remain stable, react or decompose under the depolymerization conditions. Thus, the vapor stream which is removed from the depolymerization section does not only comprise water and epsilon-caprolactam, but also impurities.

The depolymerization reaction is preferably conducted at a temperature of at least 180° C. but not higher than 400° C. The preferred temperature range for the depolymerization reaction is from 200° C. to 350° C., more preferably from 220° C. to 340° C., and most preferably from 240° C. to 325° C. Generally, the rate of epsilon-caprolactam formation increases at elevated temperatures. Temperatures lower than 400° C. are preferred since at temperatures above 400° C. side reactions of Nylon 6 and reactions of impurities occur more frequently which will result in formation of a more diverse and/or a larger set of impurities. Part of these impurities will end-up in the epsilon-caprolactam-comprising product stream that is discharged from the depolymerization reactor(s). In a preferred embodiment of the invention, the depolymerization of the pre-concentrated Nylon 6-containing material is conducted at temperatures ranging from 220° C. to 340° C. or from 240° C. to 325° C. This temperature range has resulted in particularly pure epsilon-caprolactam being obtainable after purification of the obtained crude product.

The depolymerization of Nylon 6 is achieved under wet conditions, i.e., in the presence of water, which preferably is in the form of steam, in particular superheated steam.

Preferably, superheated steam with a temperature between 100° C. and 600° C. is charged to the depolymerization reactor(s). Preferably, the superheated steam that is charged to the depolymerization reactor(s) has a temperature of at least the melting temperature of Nylon 6. Preferably, the energy content of the superheated steam that is charged to the depolymerization reactor(s) is sufficiently high that no other heat input is needed for performing the depolymerization reaction and evaporating the formed epsilon-caprolactam. In a preferred embodiment of the invention, the depolymerization section is charged with super-heated steam having a temperature ranging of from 220° C. to 575° C. In an even more preferred embodiment of the invention, the depolymerization section is charged with super-heated steam having a temperature ranging of from 275° C. to 500° C.

The depolymerization of the pre-concentrated Nylon 6-containing material in the presence of steam can be performed with the presence of additional depolymerizing agents, such as ammonia, amines or alcohols including methanol and ethanol.

Most preferably the depolymerization is carried out in the presence of a catalyst. Preferably, the used catalyst is a (Lewis or Brønsted) acid or base. The acid catalyst can in particular be selected from the group consisting of orthophosphoric acid, p-toluenesulfonic acid, boric acid, sulfuric acid, organic acid, organic sulfonic acid including xylenesulfonic acid, 4-sulfoisophthalic acid and other sulfonated aromatic hydrocarbons, solid acid, salts of the aforementioned acids, $Al_2O_3$ and $SiO_2$, and combinations thereof. The base catalyst can, e.g., be selected from the group consisting of alkali hydroxide, alkali salt, alkaline earth hydroxide and alkali such as earth salts, organic bases and solid bases, and combinations thereof. Preferably, orthophosphoric acid, boric acid, organic acid, alkali hydroxides and alkali salts are used as catalysts. More preferably, orthophosphoric acid, sodium phosphate, potassium phosphate, sodium hydroxide, potassium hydroxide, sodium carbonate, potassium carbonate, sodium hydrogen carbonate, potassium hydrogen carbonate are used. More preferably, orthophosphoric acid, p-toluenesulfonic acid, boric acid and sodium hydroxide are used. In one particularly preferred embodiment, orthophosphoric acid is used as catalyst for the depolymerization, in another, p-toluenesulfonic acid is used.

Although aforementioned (Lewis or Brønsted) acids or bases are called 'catalysts' it is known that several of them are consumed during the depolymerization reaction so that by-products are formed. For example, it is known that phosphoric acid is consumed during the depolymerization of Nylon 6 with steam, whereby phosphorus-containing by-products are produced. Generally, these phosphorus-containing by-products are ineffective as catalyst and represent a loss of valuable catalytic activity. Moreover, especially at higher temperatures several catalysts like $H_3PO_4$ have a tendency to polymerize and (partially) lose their catalytic activity.

In another preferred embodiment of the invention, however, no catalyst is used for the depolymerization of the pre-concentrated Nylon 6-containing material. This has the advantage of lower costs (both for the catalyst and the disposal of catalyst waste). However, higher temperatures (and pressures) are usually required.

The use of a catalyst (and especially orthophosphoric acid) is that the depolymerization reaction already starts at lower temperatures and can be performed under atmospheric conditions. A suitable concentration of catalyst used for the depolymerization of Nylon 6 to epsilon-caprolactam is known to the skilled person and can easily be determined by routine experimentation. If the concentration of the used catalyst is too low, the reaction rate is slow. On the contrary, if the concentration of the used catalyst is too high, the reaction is fast, but also side reaction(s) increase. Moreover, the catalyst costs are increased, which is economically disadvantageous. Typically, the catalyst content is from 0.01 to 100 wt. % relative to the Nylon 6 contained in the depolymerization reactor. Preferably, the catalyst content is from 0.1 to 50 wt. %. The optimum catalyst concentration depends on the type of catalyst that is applied for the depolymerization of Nylon 6. For the catalyst orthophosphoric acid, the preferred content is from 0.1 to 25 wt. %, more preferred from 1 to 20 wt. %. The preferred content for the catalyst p-toluenesulfonic acid is from 10 to 35 wt. %.

The depolymerization of Nylon 6 can be performed in a batch mode, in a semi-continuous mode or in a continuous mode, all of which are known to the skilled person. The terms "batch mode", "semi-continuous mode" and "continuous mode", as used herein, refer to the mode in which the Nylon 6-containing feed stock, i.e., the pre-concentrated Nylon 6-containing material, which is enriched in Nylon 6 (and optionally catalyst) is charged to the depolymerization reactor and to the mode in which the residual material is discharged from the depolymerization reactor. Typically, the residual material comprises non-Nylon 6 compounds, non-depolymerized Nylon 6, epsilon-caprolactam, catalyst and decomposition products of these components.

In a preferred embodiment, the Nylon 6 depolymerization is performed in the batch mode. In the batch mode, the feed stock, i.e., the pre-concentrated Nylon 6-containing material, which is enriched in Nylon 6, and optionally catalyst are initially charged to the depolymerization reactor. Subsequently, superheated steam is charged to the depolymerization reactor and epsilon-caprolactam is discharged from the depolymerization reactor as vapor stream comprising epsilon-caprolactam and water. Next, charging of the superheated steam to the depolymerization reactor is interrupted. After removing residual material from the depolymerization reactor, a new cycle is started by charging feed stock (and optionally catalyst) to the depolymerization reactor. In a preferred embodiment, residual material is not removed in between every cycle.

In a particular advantageous embodiment, the Nylon 6 depolymerization is performed in the continuous mode. In the continuous mode, the Nylon 6-containing feedstock (and optionally catalyst) is continuously charged to the depolymerization reactor. At the same time, superheated steam is continuously charged to the depolymerization reactor and epsilon-caprolactam is continuously discharged from the depolymerization reactor as vapor stream comprising epsilon-caprolactam and water. In addition, residual material is continuously discharged from the depolymerization reactor. Preferably, the Nylon 6-containing feedstock (and optionally catalyst) is charged as a melt, solid pieces, a slurry or a solution. More preferably, the Nylon 6-containing feed stock (and optionally catalyst) is charged as a melt, a slurry or a solution.

In a preferred embodiment, the Nylon 6 depolymerization is performed in the semi-continuous mode. In the semi-continuous mode, Nylon 6-containing feedstock (and optionally catalyst) is intermittently charged to the depolymerization reactor, while superheated steam is continuously charged to the depolymerization reactor and epsilon-caprolactam is continuously discharged from the depolymerization reactor as a vapor stream comprising epsilon-caprolactam and water. Residual material is intermittently discharged from the depolymerization reactor in the semi-continuous mode of Nylon 6 depolymerization.

The epsilon-caprolactam exits the depolymerization section in the form of a vapor stream comprising water and epsilon-caprolactam in a weight to weight ratio of from 1:1 to 50:1, preferably from 2:1 to 10:1, more preferably from 3:1 to 8:1. Preferably, the epsilon-caprolactam in the vapor stream has a pressure of 0.02 to 10 MPa, more preferably of 0.08 to 1.5 MPa, or most preferably of 0.1 to 0.5 MPa.

The Recovery Step c)

In the recovery section, epsilon-caprolactam is recovered from the epsilon-caprolactam-comprising vapor stream that is discharged from the depolymerization section. Preferably, this recovery is performed by a (partial) condensation of the vapor stream.

The epsilon-caprolactam-containing vapor stream that is discharged from the depolymerization section comprises epsilon-caprolactam, water and impurities. The epsilon-caprolactam can be separated from the remaining components of the vapor stream by sending the vapor stream from the depolymerization reactor, usually overhead, to a (preferably partial) condenser to obtain a condensate containing epsilon-caprolactam.

Preferably, the epsilon-caprolactam is separated from the remaining components of the vapor stream by sending the product stream from the depolymerization reactor, preferably overhead, to a distillation column from which a water-rich phase is obtained as top-product and an epsilon-caprolactam-rich phase as bottom product.

The epsilon-caprolactam recovered in the recovery section is crude since it contains impurities such as Nylon 6 decomposition products or other impurities stemming from non-Nylon 6 components of the multi-component starting material. The crude epsilon-caprolactam that is recovered in step c) comprises water and epsilon-caprolactam, preferably it is an aqueous solution comprising epsilon-caprolactam. Thus, the crude epsilon-caprolactam recovered in the recovery section requires additional purification to yield high purity epsilon-caprolactam. "Crude" as used herein, can therefore be defined as being less pure than the purified epsilon-caprolactam obtained as the product of the process of the invention.

Preferably, the crude epsilon-caprolactam comprises epsilon-caprolactam in the range of from 6 wt. % to 95 wt. %, more preferably from 20 wt. % to 90 wt. %, and most preferably from 40 wt. % to 75 wt. %. The remainder is mainly water.

The Purification Step d)

In step d), the crude epsilon-caprolactam which is obtained in the recovery section [C] is purified in the purification section [D] to yield high purity epsilon-caprolactam.

Optionally, the crude epsilon-caprolactam is filtered before being charged to the purification section. The filtration ensures the removal of undissolved impurities which could otherwise hinder the further purification process.

Purified epsilon-caprolactam is obtained from the crude epsilon-caprolactam by first extracting in step (i) the crude epsilon-caprolactam with an organic solvent, whereby an aqueous phase and an organic phase comprising the organic solvent, epsilon-caprolactam and impurities are obtained. The organic solvent with which the crude epsilon-caprolactam is extracted is preferably an aromatic hydrocarbon, an aliphatic hydrocarbon, a cycloaliphatic hydrocarbon, a halogenated hydrocarbon and/or a $C_4$-$C_{10}$ aliphatic or cycloaliphatic alcohol. Optionally, the organic solvent with which the crude epsilon-caprolactam is extracted is preferably a mixed extractant which consists of an aromatic hydrocarbon, an aliphatic hydrocarbon, a cycloaliphatic hydrocarbon, a halogenated hydrocarbon and/or a $C_4$-$C_{10}$ aliphatic or cycloaliphatic alcohol, and a $C_5$-$C_8$ alkane or $C_5$-$C_8$ cycloalkane. Particularly good results are achieved if the organic solvent for extraction of the crude epsilon-caprolactam is selected from the group consisting of cyclohexane, benzene, toluene, methylene chloride, chloroform, trichloroethane, 4-methyl-2-pentanol (a.k.a. MIBC, methyl isobutyl carbinol), 1-octanol, 2-ethylhexanol and mixtures thereof. More preferably, the organic solvent for extraction of the crude epsilon-caprolactam is selected from the group consisting of benzene, toluene, alcohols, and mixtures thereof. Still more preferably, the organic solvent for extraction of the crude epsilon-caprolactam is selected from the group consisting of toluene, 1-octanol, 4 methyl-2 pentanol, 2-ethylhexanol and mixtures thereof. Typically, the weight ratio of organic solvent to epsilon-caprolactam is from 0.01:1 to 40:1, preferably from 0.01:1 to 20:1, more preferably from 0.05:1 to 10:1 and most preferably from 0.1:1 to 5:1.

Optionally, the organic solvent for extraction of the crude epsilon-caprolactam is mixed with an alkane, $C_mH_{2m+2}$ wherein m is 5 to 8, a cycloalkane or $C_mH_{2m}$ wherein m is 5 to 8 so that a mixed extraction agent is formed. Particularly good results are achieved if the alkane or cycloalkane is present in the mixed extraction agent in the range of from 5 to 90% and preferably from 25 to 75% by weight of the total weight of the mixed extraction agent.

In an embodiment of the invention, in which the organic solvent has a lower density than the crude epsilon-caprolactam, the extraction with organic solvent in step d)(i) is carried out in a counter-current operated extraction column whereby the crude epsilon-caprolactam to be purified is introduced at the top and the organic solvent at the bottom of the column. The extraction results in an aqueous phase and an organic phase comprising the organic solvent, epsilon-caprolactam and impurities, with a weight ratio of impurities to epsilon-caprolactam that is reduced compared to the weight ratio of impurities to epsilon-caprolactam in the crude epsilon-caprolactam. So, as a consequence of this extraction, the epsilon-caprolactam is purer than before the extraction.

In another preferred embodiment of the invention, in which the organic solvent has a higher density than the crude epsilon-caprolactam, the extraction with organic solvent in step d)(i) is carried out in a counter-current operated extraction column, whereby the crude epsilon-caprolactam to be purified is introduced at the lower part and the organic solvent at the upper part of the column. The extraction results in an aqueous phase comprising water and impurities, and an organic phase comprising the organic solvent, epsilon-caprolactam and impurities, with a weight ratio of impurities to epsilon-caprolactam that is reduced compared to the weight ratio of impurities to epsilon-caprolactam in the crude epsilon-caprolactam. So, as a consequence of this extraction, the epsilon-caprolactam is purer than before the extraction.

Optionally, the organic phase comprising the organic solvent, epsilon-caprolactam and impurities is washed with water or with an aqueous alkaline solution before entering step d)(iii). If washing is performed with an aqueous alkaline solution, the alkaline solution is preferably an aqueous solution comprising an alkali metal hydroxide and/or alkali metal carbonate, preferably sodium hydroxide or potassium hydroxide. Said alkali metal hydroxide solution preferably comprises 0.5 to 2.0 wt. % of sodium hydroxide or potassium hydroxide.

The skilled person can determine by routine experimentation the amount of water or aqueous alkaline solution necessary for efficient washing of the organic phase comprising the organic solvent, epsilon-caprolactam and impurities. Typically, this amount is between 0.1 and 5 wt. % relative to the amount of organic solvent excluding epsilon-caprolactam dissolved in the to-be-washed organic phase. Preferably, the washing of the organic phase comprising the organic solvent, epsilon-caprolactam and impurities with water or aqueous alkaline solution is carried out in a counter-current operated washing column whereby the organic phase comprising the organic solvent, epsilon-caprolactam and impurities is introduced at the bottom and the water or aqueous alkaline solution at the top of the column. The washing results in a washed organic phase comprising the organic solvent, epsilon-caprolactam and impurities and a residue-comprising phase. Usually the residue-comprising phase contains water and epsilon-caprolactam and only some minor impurities. As a consequence of the washing, the impurity content of the washed organic phase is reduced compared to the impurity content of the organic phase before washing.

Optionally, prior to step d)(iii) of the process of the invention, in which purified epsilon-caprolactam is obtained by distillative removal of impurities with lower or higher boiling points than epsilon-caprolactam, one or more process steps are included to reduce the energy consumption of the purification step d) of the process of the invention, to enhance the quality of the purified epsilon-caprolactam and/or to simplify the distillative removal of impurities with lower- or higher-boiling points than epsilon-caprolactam.

Optionally, according to step d)(ii) of the process of the invention, the obtained organic phase comprising the organic solvent, epsilon-caprolactam and impurities, that is optionally washed with water or with an aqueous alkaline solution, is solvent switched, whereby the organic solvent in the organic phase comprising the organic solvent, epsilon-caprolactam and impurities is replaced by water and whereby an aqueous phase comprising water, epsilon-caprolactam and impurities with lower- or higher-boiling points than epsilon-caprolactam is obtained and wherein the solvent switch process is selected from processes based on back-extraction (a.k.a. reextraction) with water, and processes based on solvent swap distillation, whereby the organic solvent is distilled off and water is charged. The term "replaced" as used herein means that at least 60%, preferably at least 80% and most preferably at least 90, 95 or 98% by weight of the organic solvent present in the organic phase comprising the organic solvent, epsilon-caprolactam and impurities is replaced by water.

Two solvent switch alternatives are described in the following.

Solvent Switch: First Alternative:

Optionally, the epsilon-caprolactam-solvent phase that is optionally washed is subsequently reextracted with water, whereby an epsilon-caprolactam-water phase is obtained. Preferably, consequently, this epsilon-caprolactam-water phase is stripped and/or distilled to remove residual solvent. Although the amount of the water used for the recovery of epsilon-caprolactam is not critical, the amount of the water used is usually 0.5 to 20 times by weight based on the recovered epsilon-caprolactam. Preferably, it is 0.75 to 10 times by weight, more preferably 1 to 5 times by weight.

The reextraction with water can advantageously be carried out in a counter-current operated extraction column, the epsilon-caprolactam-solvent phase to be purified being introduced at the bottom and the water at the top of the column. The reextraction results in an epsilon-caprolactam-water phase and results in a solvent phase that comprises impurities. Usually the solvent phase that comprises impurities is, optionally after purification, preferably by distillation, re-used.

In another preferred embodiment, in which the organic phase comprising the organic solvent, epsilon-caprolactam and impurities, that has been optionally washed, has a lower density than water, the organic phase is introduced at the lower part of the extraction column and the water at the upper part of the extraction column. The back-extraction results in an organic solvent phase that comprises impurities, and in an aqueous phase comprising water, epsilon-caprolactam and impurities with lower- or higher-boiling points than epsilon-caprolactam, with a weight ratio of impurities to epsilon-caprolactam that is reduced compared to the weight ratio of impurities to epsilon-caprolactam in the organic phase comprising the organic solvent, epsilon-caprolactam and impurities prior to the back-extraction. Thus, because of the back-extraction, purer epsilon-caprolactam is obtained. Preferably, the organic solvent phase that comprises impurities is, optionally after purification (preferably by distillation), re-used.

In another preferred embodiment, in which the organic phase comprising the organic solvent, epsilon-caprolactam and impurities has a higher density than water, the organic phase is introduced at the upper part of the extraction column and the water at the lower part of the extraction column. The back-extraction results in an organic solvent phase that comprises impurities, and in an aqueous phase comprising water, epsilon-caprolactam and impurities with lower- or higher-boiling points than epsilon-caprolactam, with a weight ratio of impurities to epsilon-caprolactam that is reduced compared to the weight ratio of impurities to epsilon-caprolactam in the organic phase comprising the organic solvent, epsilon-caprolactam and impurities prior to the back-extraction. Thus, because of the back-extraction, the epsilon-caprolactam is purer than before the back-extraction. Preferably, the organic solvent phase that comprises impurities is, optionally after purification (preferably by distillation), re-used.

The resulting epsilon-caprolactam-water phase, that was optionally stripped and/or distilled to remove residual solvent, is concentrated by evaporation of water, whereby a concentrated aqueous epsilon-caprolactam phase is obtained. The epsilon-caprolactam content of this aqueous epsilon-caprolactam phase is usually between 50 and 99.9 wt. % relative to the entire phase.

Solvent Switch: Second Alternative:

Optionally, organic solvent is evaporated from the epsilon-caprolactam-solvent phase that is optionally washed instead of being reextracted with water. Any suitable evaporation vessel may be used, for example a column. Preferably the evaporation is performed in the presence of water. More preferably the evaporation is performed as an azeotropic distillation in which case the organic solvent is evaporated as an azeotropic mixture. The evaporation results in epsilon-caprolactam product. Typically, the epsilon-caprolactam product is an aqueous epsilon-caprolactam phase. The epsilon-caprolactam content of this aqueous epsilon-caprolactam phase is usually between 50 and 99.9 wt. % relative to the entire phase.

The solvent switch process can also be a process based on solvent swap distillation, whereby the organic solvent is distilled off and water is charged. In a preferred embodiment, the solvent switch process is a process based on solvent swap distillation that is performed as a single-stage process, whereby the organic solvent is distilled off from the organic phase comprising the organic solvent, epsilon-caprolactam and impurities, and water is charged. More preferably, the solvent switch is performed as an azeotropic distillation with water addition in which case the organic solvent is evaporated as an azeotropic mixture comprising organic solvent and water. The purpose of the azeotropic distillation is to remove organic solvent and to add water. Preferably, substantially all of the organic solvent is removed. "Substantially all" in this context means that at least 90%, preferably at least 95% and most preferably at least 98 or 99% by weight of the organic solvent present in the organic phase comprising the organic solvent, epsilon-caprolactam and impurities is removed. Preferably, the water is added as a liquid. More preferably, water, in the liquid state, is added to the upper part of the distillation column as reflux. Even more preferably, a part of the water that is added as reflux is obtained by condensation of the azeotropic mixture that is distilled off in the distillation column.

Any suitable vessel may be used for the solvent switch process, for example a column, preferably a distillation column that is operated in a continuous mode. The distillation column may include trays, packing or a combination thereof.

In another preferred embodiment, the solvent swap distillation is performed as a two-stage process. The first stage is a pre-concentration stage and the second stage is the actual solvent swap distillation.

The organic phase comprising the organic solvent, epsilon-caprolactam and impurities is charged to the first stage. In the first stage, a first fraction of the organic solvent is removed by distillation from the organic phase comprising the organic solvent, epsilon-caprolactam and impurities at the upper part of the distillation column. Preferably, this distillation is performed under reflux. Under reflux means that organic solvent, in the liquid phase, is charged to the upper part of the distillation column. More preferably a part of the organic solvent that is removed by distillation at the upper part of a distillation column is, after condensation, charged as a liquid to the upper part of the distillation column. The remaining organic phase comprising the organic solvent, epsilon-caprolactam and impurities is discharged from the first stage and charged to the second stage. Due to distillation in the first stage, the chemical composition of the remaining organic phase comprising the organic solvent, epsilon-caprolactam and impurities is different from the organic phase comprising the organic solvent, epsilon-caprolactam and impurities that is charged to the first stage. Generally, compared to the organic phase comprising the organic solvent, epsilon-caprolactam and impurities that is charged to the first stage, the remaining organic phase comprising the organic solvent, epsilon-caprolactam and impurities contains a higher amount in percent weight of epsilon-caprolactam and compounds with a higher boiling point than epsilon-caprolactam and a lower percent in weight of compounds with a boiling point lower than epsilon-caprolactam.

In the second stage, the remaining organic solvent is distilled off from the remaining organic phase comprising the organic solvent, epsilon-caprolactam and impurities, and water is charged. More preferably, in the second stage, the solvent switch is performed as an azeotropic distillation with water addition in which case the organic solvent is evaporated as an azeotropic mixture comprising organic solvent and water.

Any suitable vessel may be used in each stage for the solvent switch, for example a column, preferably a distillation column that is operated in a continuous mode. The distillation column may include trays, packing or a combination thereof.

The solvent swap distillation (either performed as a single-stage process or as a two-stage process) results in an aqueous phase comprising water, epsilon-caprolactam and impurities with lower- or higher-boiling points than epsilon-caprolactam and optionally residual organic solvent. Preferably, the epsilon-caprolactam content of this aqueous phase is between 25 and 99.9%, more preferably between 50 and 99.5% and most preferably between 85 and 99% by weight relative to the entire aqueous phase.

Therefore, according to a particular advantageous embodiment of the invention, after the extraction of the crude epsilon-caprolactam in step d)(i), the purification in step d) also comprises the step of (ii) solvent switching based on solvent swap distillation.

Optionally, subsequently the aqueous epsilon-caprolactam phase that is obtained according to the process of the first or the second solvent switch alternative is oxidized and/or treated with ion exchange resin and/or hydrogenated.

In a preferred embodiment, an oxidant, e.g., potassium permanganate, sodium permanganate, and/or hydrogen peroxide, is added to the aqueous epsilon-caprolactam phase. Most preferably, potassium permanganate is used as oxidant.

Preferably, the oxidant is added in the form of an aqueous solution to the aqueous epsilon-caprolactam phase, so that a dilute aqueous solution is obtained during purification by oxidation. The oxidant can also be added as a solid. The oxidant can also be added as a slurry. The skilled person can determine by routine experimentation the amount of oxidant necessary for efficient oxidation of the aqueous epsilon-caprolactam phase. The exact amount of oxidant is, amongst others, very much dependent on the composition of the Nylon 6 streams that are charged to the depolymerization section in this process of the invention. Preferably, the amount of oxidant is between 0.01 and 5% by weight relative to the amount of epsilon-caprolactam dissolved in the to-be-oxidized aqueous phase.

The temperature used for oxidation of the aqueous solution in the process of the invention can vary. Preferably, oxidation of this aqueous solution with an oxidant is performed at a temperature ranging from 20° C. to 85° C., more preferably ranging from 30° C. to 80° C., wherein the oxidant is selected from the group consisting of potassium permanganate, sodium permanganate and hydrogen peroxide and combinations thereof, in particular potassium permanganate.

The length of time used for oxidation with an oxidant can vary. Preferably, in the process of the invention, oxidation of the aqueous epsilon-caprolactam phase with an oxidant is performed for 1 minute to 24 hours, more preferably for 2 minutes to 6 hours, and most preferably for 5 minutes to 2 hours.

The concentration of epsilon-caprolactam in the aqueous epsilon-caprolactam phase used for oxidation with an oxidant can vary. Preferably, the aqueous solution used for oxidation comprises a weight to weight ratio of epsilon-caprolactam to water from 5:1 to 1:5, more preferably from 3:1 to 1:3 and, most preferably from 2:1 to 1:2. Optionally, prior to the addition of the oxidant to the aqueous phase, the weight to weight ratio of epsilon-caprolactam to water is adapted. Preferably, the weight to weight ratio of epsilon-caprolactam to water is adapted by either addition of water or by removal of water.

In case potassium permanganate and/or sodium permanganate is used as oxidant, solid manganese(IV) oxide ($MnO_2$) particles are formed as reaction product. The skilled person can determine by routine experimentation the optimal solid-liquid filtration procedure for efficient removal of solid manganese(IV) oxide particles from the aqueous phase after oxidation. The usage of filter aids, like activated carbon particles or kieselguhr, to improve the filtration procedure are in this regard common practice.

In another preferred embodiment, the aqueous epsilon-caprolactam phase is treated with ion exchange resin. Optionally, the aqueous epsilon-caprolactam phase is first treated with an acidic cation exchange resin, and subsequently with a basic anion exchange resin. Optionally, the aqueous epsilon-caprolactam phase is first treated with a basic anion exchange resin, and subsequently with an acidic cation exchange resin. Preferably, cation exchange resin is a sulfonated polystyrene or a styrene-divinylbenzene copolymer and the anion exchange resin is a quaternary ammonium group-containing polystyrene or an exchange resin having secondary or tertiary amino groups. The treatment temperature of the aqueous epsilon-caprolactam solution may be preferably 15° C. to 100° C., more preferably 35° C. to 70° C. For performing efficiently adsorption-separation of the impurities at cation exchange resin and anion exchange resin, the concentration of the aqueous epsilon-caprolactam solution to be treated may be preferably 5 to 90%, more preferably 5 to 70%. The skilled person can determine by routine experimentation the optimal (combination of) ion exchange resin(s) and the amount of ion exchange resin(s) for efficient removal of impurities from the aqueous epsilon-caprolactam phase and the regeneration of the loaded ion exchange resin(s).

In another preferred embodiment, the aqueous epsilon-caprolactam phase is hydrogenated in the presence of a hydrogenation catalyst known per se. The hydrogenation can advantageously be carried out as for example described in EP635487.

The hydrogenation temperature is generally between 20° C. and 160° C. As a rule a not too low temperature will be chosen, for at a low temperature the reaction time is longer. The temperature is as a rule not too high because high temperatures have a negative influence on the epsilon-caprolactam quality. The temperature therefore preferably is between 70° C. and 130° C., and most preferably between 80° C. and 100° C.

The hydrogenation pressure may be between 0.1 MPa and 15 MPa. High pressures are advantageous as they allow dissolution of a larger quantity of hydrogen in the water-epsilon-caprolactam mixture. Since the impurity content is normally not so high as to necessitate a large quantity of hydrogen, an excessively high pressure is not needed. Very high pressures further have the drawback that expensive process equipment is needed. As a rule, therefore, the pressure is between 0.3 MPa and 5 MPa.

The hydrogenation catalysts may be any known heterogeneous hydrogenation catalyst. Examples of such catalysts are ruthenium on aluminium oxide, rhodium on aluminium oxide, platinum on carbon, palladium on carbon, Raney nickel, nickel on silica and nickel on aluminium oxide. Preferably, use is made of nickel-containing catalysts.

Suitable nickel catalysts as a rule have a nickel content between 5 and 80 wt. %, relative to the metal and the support. Besides nickel the catalyst may contain some activators such as Zr, Mn, Cu or Cr. The activator content is generally between 1 and 20 wt. %. If palladium-containing heterogeneous catalysts are used, the palladium content will generally be between 0.01 and 10 wt. %.

Optionally water is evaporated from the, optionally oxidized and/or treated with ion exchange resin and/or hydrogenated, aqueous epsilon-caprolactam phase. Following the oxidation and/or hydrogenation and/or evaporation of water, the aqueous epsilon-caprolactam phase is distilled to recover high purity epsilon-caprolactam and a distillation residue.

In a preferred embodiment of the process of the invention, prior to the distillative removal in step d)(iii) an aqueous phase comprising water, epsilon-caprolactam and impurities with lower- or higher-boiling points than epsilon-caprolactam is obtained by
  at least partially replacing the organic solvent with water, and wherein the solvent replacement step is selected from a process based on reextraction with water, and a process based on solvent replacement distillation, in which the organic solvent is distilled off and water is charged; and optionally followed by oxidation by an oxidant selected from potassium permanganate, sodium permanganate and hydrogen peroxide; and/or optionally followed by treatment with an acidic cation exchange resin and/or a basic anion exchange resin; and/or optionally followed by hydrogenation in the presence of a hydrogenation catalyst selected from Raney nickel, nickel on silica, nickel on aluminium oxide, ruthenium on aluminium oxide, rhodium on aluminium oxide, platinum on carbon and palladium on carbon.

In step d)(iii) of the process of the invention purified epsilon-caprolactam is obtained by distillative removal of impurities with lower- or higher-boiling points than epsilon-caprolactam. Typically, distillation of the optionally washed organic phase comprising the organic solvent, epsilon-caprolactam and impurities is carried out at a reduced pressure. In an embodiment of the invention, the distillation is effected at a pressure of less than 50 kPa, preferably less than 20 kPa and more preferably less than 10 kPa. Preferably, the distillation temperature at the bottom of the distillation column is between 100° C. and 200° C. and more preferably between 110° C. and 180° C. The distilling includes separating low-boiling organic impurities (having a lower boiling point than epsilon-caprolactam) and/or separating organic high-boiling impurities (having a higher boiling point than epsilon-caprolactam) from epsilon-caprolactam.

In a preferred embodiment of the invention, prior to the distillative removal in step d)(ii), alkali metal hydroxide, preferably NaOH, is added to the organic phase. Preferably, the amount of NaOH that is added ranges from 0.5 to 150 mmol, more preferably and most preferably from 2 to 80 mmol per kg e caprolactam. This leads to a particularly effective distillative removal of impurities with lower and higher boiling points than epsilon-caprolactam in the subsequent distillation.

The purification of the crude epsilon-caprolactam in the purification section according to the invention typically comprises the following steps:

(i) extracting the crude epsilon-caprolactam with an organic solvent, whereby an aqueous phase and an organic phase are obtained, and wherein the organic phase comprises the organic solvent, epsilon-caprolactam and impurities;

(ii) optionally, switching the solvent by replacing the organic solvent at least partially with water, whereby an aqueous phase comprising water, epsilon-caprolactam and impurities with lower- or higher-boiling points than epsilon-caprolactam is obtained and wherein the solvent switch step (ii) is selected from a process based on back-extraction with water, and a process based on solvent swap distillation, in which the organic solvent is distilled off and water is charged; and (iii) obtaining purified epsilon-caprolactam by distillative removal of impurities with lower- or higher-boiling points than epsilon-caprolactam.

In a preferred embodiment of the invention, crude epsilon-caprolactam obtained from a Beckmann rearrangement of cyclohexanone oxime is also purified in the purification section apart from the crude epsilon-caprolactam that is recovered in the recovery section. This has the advantage that by introducing recycled epsilon-caprolactam according to the present invention, the carbon footprint of a plant producing epsilon-caprolactam de novo from a Beckmann rearrangement of cyclohexanone oxime can be reduced.

The high purity epsilon-caprolactam obtained according to the method of the invention can be used to make Nylon 6 using processes well-known to the skilled person. The Nylon 6 may then be used in all known materials, including engineering materials, fibers and films.

The Plant

The invention also provides the plant in which the above-described process of the invention can be carried out. All apparatus features specifically described in connection with the plant below therefore also apply as specific embodiments of the process of the invention and vice versa. I.e., the plant is suitable for carrying out the process of the invention. Thus, it is to be understood that what has been described in connection with the process of the invention equally applies to the plant embodiments.

The plant can correspond to a laboratory setup as in the examples. Preferably, however, the plant is an industrial scale plant. "Industrial scale" means that the plant has a production capacity for epsilon-caprolactam (i.e., is in principle capable of producing the same in an amount of) of at least 500 tons/year if operated all the time.

The plant of the invention is suitable for the production of purified epsilon-caprolactam from Nylon 6-containing multi-component material and comprises at least the following four sections: (A) a Nylon 6-pre-concentration section, (B) a depolymerization section, (C) a recovery section, and (D) a purification section. These sections, and thereby the plant, is configured to carry out the process of the invention described above.

In addition, the plant can comprise a mechanical size reduction section [O] to fragment the Nylon 6-containing multi-component material into pieces and/or a washing section [W] to wash the Nylon 6-containing multi-component material. The mechanical size reduction section [O] comprises equipment for the mechanical fragmentation of the Nylon 6-containing multi-component material into pieces. Non-limiting examples of this fragmentation equipment are a cutter, shredder, mill, grinder or chipper.

The Nylon 6-pre-concentration section [A] comprises extraction equipment in which the Nylon 6-containing multi-component material is extracted with one or more organic solvents. The extraction equipment can have any desirable form such as mixer-settler extractors, extraction columns and/or centrifugal extraction equipment and is optionally operated under pressure. The pieces of Nylon 6-containing multi-component material are preferably mixed with the organic solvent in the extraction equipment of the Nylon 6-pre-concentration section by a stirrer. The Nylon 6-pre-concentration section may comprise further units, in particular such that allow for storage, recovery and purification of one or more organic solvents that are applied in this section, and for collection and intermediate storage of the obtained mainly non-Nylon 6 containing by-product that is formed in this section and the desired pre-concentrated Nylon 6-containing material.

The depolymerization section [B] comprises one or more depolymerization reactors that are operated in series and/or in parallel. The Nylon 6-containing multi-component material is fed to the reactor as a solid or as a melt, preferably as a melt. This feeding may be achieved by using an extruder, gear pump, or other means known in the art.

During production, a depolymerization reactor is at least partially filled with Nylon 6-containing feed stock, residual material, epsilon-caprolactam (and optionally catalyst). The depolymerization reactor can have any desirable form. Preferred reactor types are stirred and non-stirred bubble column reactors, stirred reactors and extruder type reactors.

The depolymerization reactor must be equipped with facilities for feeding of the Nylon 6-containing multi-component material, the superheated steam and optionally the catalyst. In addition, the depolymerization reactor must be equipped with facilities for discharging the vapor stream comprising epsilon-caprolactam and water, and the residual material.

Good contact between steam and the reactor content is essential for an effective operation. Such contact may be achieved by various means known generally in the art. As an example, steam may be sparged through the material using a multiplicity of inlets, for example, using a steam distributor. Improved contact may be achieved by including mechanical agitation in the reactor, for example, using a combination of rotating paddles and static fins.

Usually, depolymerization will be complete in 0.5 to 6 hours.

If super-heated steam at high temperatures is not available on a production site, it must be made on-purpose by super-heating of available steam from a boiler in a so-called super-heater.

The recovery section [C] comprises one or more (preferably partial) condensers to which the vapor stream comprising epsilon-caprolactam and water is charged. Such a (partial) condenser can have any desirable form. Preferably, the condenser is a distillation column from which a water-rich phase is obtained as top-product and an epsilon-caprolactam-rich phase as bottom product.

The purification section [D] comprises one or more pieces of extraction equipment, optionally one or more pieces of solvent switch equipment, optionally an oxidation section, optionally a hydrogenation section and one or more pieces of distillation equipment, to which the crude epsilon-caprolactam is charged and from which high purity epsilon-caprolactam is discharged.

To the extraction equipment, crude epsilon-caprolactam and the organic solvent are charged and an organic phase comprising the organic solvent, epsilon-caprolactam and impurities, and an aqueous phase comprising water and impurities are discharged. The extraction equipment is selected from mixer-settler extractors, extraction columns, centrifugal extractors, and combinations thereof. Preferably, extraction equipment is a static or an agitated extraction column, like KARR® Columns, SCHEIBEL®, rotating disc contactors (RDC), pulsed columns, sieve trays (static) columns, random packing (static) columns, and structured packing (SMVP) (static) columns.

To the solvent switch equipment water and an organic phase comprising the organic solvent, epsilon-caprolactam and impurities are charged and an organic solvent and an epsilon-caprolactam-water phase comprising water, epsilon-caprolactam, and impurities are discharged. The solvent switch equipment for processes based on reextraction is selected from mixer-settler extractors, extraction columns, centrifugal extractors, and combinations thereof. Preferably, equipment for reextraction is a static or an agitated extraction column, like KARR® Columns, SCHEIBEL® Columns, rotating disc contactors (RDC), pulsed columns, sieve trays (static) columns, random packing (static) columns, and structured packing (static) columns.

The solvent switch equipment for processes based on solvent swap distillation is preferably selected from sieve trays distillation columns, random packing distillation columns, and structured packing distillation columns. Preferably, the distillation column is equipped with a reboiler, a condenser and equipment for reflux. The distillation column can be operated at atmospheric pressure, sub-atmospheric pressure or super-atmospheric pressure. Preferably, water is charged to the upper part of the distillation column and the aqueous phase comprising water, epsilon-caprolactam and impurities with lower- or higher-boiling points than epsilon-caprolactam is discharged from the lower part of the distillation column.

The oxidation section comprises one or more oxidation reactors that are operated in series and/or in parallel. An oxidant and the epsilon-caprolactam-water phase comprising water, epsilon-caprolactam and impurities are charged to the oxidation section. Usually, the oxidant is charged as an aqueous solution or as a solid. In case potassium or sodium permanganate is applied as oxidant, the oxidation section also comprises a filtration section. The oxidation reactor can have any desirable form. Preferred reactor types are stirred and non-stirred reactors and packed column type reactors. The oxidation reactor must be equipped with facilities for feeding of the aqueous phase comprising water, epsilon-caprolactam and impurities with lower- or higher-boiling points than epsilon-caprolactam, and the oxidant. In addition, the oxidation reactor must be equipped with facilities for discharging the oxidized epsilon-caprolactam-water phase comprising water, epsilon-caprolactam, and impurities, and optionally formed solid manganese(IV) oxide ($MnO_2$) particles. Preferably, the oxidation is performed at a temperature ranging from 20° C. to 85° C. and at atmospheric conditions.

The optionally present solid manganese(IV) oxide ($MnO_2$) particles can be removed by settling or by solid-liquid filtration, preferably by solid-liquid filtration. The usage of filter aids, like activated carbon particles, to improve the filtration procedure are common practice. Filter systems suitable for the separation of solid manganese(IV) oxide particles are known to the skilled person. To such a filter system a suspension of the oxidized epsilon-caprolactam-water phase comprising the water, epsilon-caprolactam and impurities, and the solid manganese(IV) oxide particles are charged and the filtered oxidized epsilon-caprolactam-water phase comprising the water, epsilon-caprolactam and impurities is discharged. Generally, the solid manganese(IV) oxide particles are retained in the filter system. Preferably, such a filter system is operated in a semi-continuous mode, whereby the suspension and the filtered phase are continuously charged and continuously discharged, while the separated solids are collected in the filter system. From time to time, the charging of the suspension is interrupted and the collected solids are removed from the filter system.

The hydrogenation section comprises one or more hydrogenation reactors that are operated in series and/or in parallel. All types of reactors in which the hydrogenation is performed in the presence of a solid catalyst can be employed. Preferably, the hydrogenation reactor is a stirred tank reactor or a fixed bed reactor.

A hydrogen containing gas stream and the epsilon-caprolactam-water phase comprising water, epsilon-caprolactam and impurities are charged to the hydrogenation section. An epsilon-caprolactam-water phase comprising water, epsilon-caprolactam and impurities that is hydrogenated and optionally a hydrogen containing purge gas stream are discharged from the hydrogenation section. Under normal operation conditions, the hydrogenation catalyst remains in the hydrogenation reactors and is only replaced after deactivation.

To the distillation equipment the epsilon-caprolactam-water phase comprising water, epsilon-caprolactam and impurities is charged and high purity epsilon-caprolactam, water, and impurities (i.e., low-boiling organic impurities (having a lower boiling point than epsilon-caprolactam) and organic high-boiling impurities (having a higher boiling point than epsilon-caprolactam)) are discharged. The distillation equipment is selected from sieve trays distillation columns, random packing distillation columns, structured packing distillation columns, and horizontal and vertical (falling and climbing) film evaporators. Preferably, the distillation columns are equipped with a reboiler, a condenser, and equipment for reflux. The distillation equipment can be operated at atmospheric pressure, sub-atmospheric pressure or super-atmospheric pressure, preferably at sub-atmospheric pressure.

Preferably, the distillation includes the separation of water, low-boiling organic impurities (having a lower boiling point than epsilon-caprolactam) and/or organic high-boiling impurities (having a higher boiling point than epsilon-caprolactam) from epsilon-caprolactam. Preferably, the distillation includes, in a first step, the separating out of water as a top product, and the production of epsilon-caprolactam containing low-boiling impurities and high-boiling impurities as a bottom product. In a second step, low-boiling impurities are separated out as top product and epsilon-caprolactam containing high-boiling impurities is obtained as a bottom product. In a third step, high purity epsilon-caprolactam is separated out as a top product and as a bottom product a distillation residue comprising epsilon-caprolactam and high boiling impurities is produced. Optionally, the first step and the second step are combined.

Preferably, prior to the distillative removal of water and impurities, alkali metal hydroxide, preferably NaOH, is added to the oxidized epsilon-caprolactam-water phase comprising water, epsilon-caprolactam and impurities. Preferably, the amount of NaOH that is added ranges from 0.5 to 100 mmol per kg epsilon-caprolactam, and more preferably from 2 to 80 mmol per kg epsilon-caprolactam. This leads to a particularly effective distillative removal of impurities with lower and higher boiling points than epsilon-caprolactam in the subsequent distillation.

The process of the invention can be operated in a continuous, semi-continuous or batch-wise fashion. Accordingly, also the plant of the invention can be configured to allow for one or more of these operating modes. In a preferred embodiment, the plant is configured to operate the process of the invention in a continuous or semi-continuous fashion. However, a discontinuous process is also possible. For example, the plant of the invention need not contain all sections described herein in one location. In particular, the Nylon 6-pre-concentration section can be located at a first location, while the depolymerization section, the recovery section and the purification section are located at a second location. Similarly, also the mechanical size reduction section can be located at a different site.

In a particularly advantageous embodiment of the invention, the plant can comprise as purification section a purification section that is shared with a de novo synthesizing epsilon-caprolactam plant, wherein the purification section is usually or actually used to purify crude epsilon-caprolactam produced by other processes such as by Beckmann rearrangement of cyclohexanone oxime. In this way, the invention provides for the use of epsilon-caprolactam recovered from Nylon 6-containing multi-layer material for reducing the carbon footprint of an epsilon-caprolactam production plant. Proceeding in this way also has the advantage that a highly sophisticated purification section of an existing plant producing epsilon-caprolactam via a Beckmann rearrangement reaction can be used in the process of the invention. This is cost-effective, as no separate purification section needs to be built for the process and plant of the invention. It is surprising that recovered epsilon-caprolactam obtained via depolymerization of Nylon 6 that is produced from a Nylon 6-containing multi-component material can be mixed with and purified together with crude epsilon-caprolactam produced by other processes such as by Beckmann rearrangement of cyclohexanone oxime, without impairing the quality of the latter. In applicant's opinion, this is only made possible by the special combination of Nylon 6 pre-concentration, depolymerization and recovery steps of the invention, which leads to an exceptionally pure epsilon-caprolactam product that can be mixed with and purified together with epsilon-caprolactam produced by other processes such as by Beckmann rearrangement without disadvantages in terms of quality of the resulting product.

The Product

The process of the invention allows producing high-purity and therefore high-quality epsilon-caprolactam, which meets the specification for high demanding applications and at the same time is particularly economically friendly due to its lowered product carbon foot print and the use of waste as starting material. In preferred embodiments, the epsilon-caprolactam obtained by the process of the invention fulfils one or more of the following specifications, wherein the parameters and measurement methods are defined as in the Example section herein below:

PAN: max. 5
E290: max. 0.05
VB: max. 0.5 mmol/kg
Alkalinity: max. 0.1 mmol/kg
Acidity: max. 0.1 mmol/kg The epsilon-caprolactam produced by the process of the invention is particularly economical and environmentally friendly. This is evident from the much lower carbon foot print of the epsilon-caprolactam produced by the process of the invention as compared to classically produced epsilon-caprolactam (e.g., by Beckmann rearrangement of cyclohexanone oxime).

The environmental impact of a product is generally expressed as the 'product carbon footprint'. The carbon footprint of a product is defined as the total emissions caused by the formation of that product, expressed as ton carbon dioxide equivalent per ton product. The carbon footprint of a product is amongst others depending on the feed stock, auxiliary materials, energy consumption, energy sources, production process and process efficiencies. Quantification of the carbon footprint of a product can be done as described in, e.g., the European Standard EN ISO 14040:2006 ("Environmental management—Life cycle assessment—Principles and framework).

Product Carbon Footprint calculations can be done both in-house or by external (preferably) certified organizations. These organizations verify and certify the Product Carbon Footprint calculations based on e.g., LCA standard ISO 14040.

J. Hong and X. Xu ("Environmental impact assessment of caprolactam production—a case study in China"; J. of Cleaner production 27 (2012) 103-108; DOI: 10.1016/j.jclepro.2011.12.037) reported that the potential impact of "virgin" epsilon-caprolactam obtained via Beckmann rearrangement of cyclohexanone oxime on global warming is 7.5 ton $CO_2$ equivalent/ton epsilon-caprolactam, in case coal-based electricity and steam generation are involved. If natural gas-based electricity and steam generation are involved, the potential impact of virgin epsilon-caprolactam on global warming of the epsilon-caprolactam production process will be reduced to 6.4 ton $CO_2$ equivalent/ton epsilon-caprolactam.

The product carbon footprint of epsilon-caprolactam that is obtained according to the process of the invention is much lower than the one of de novo synthesized, or "virgin" epsilon-caprolactam. Preferably, the product carbon footprint of the epsilon-caprolactam that is obtained according to the process of the invention is less than 4 ton $CO_2$ equivalent/ton epsilon-caprolactam, more preferably less than 3 ton $CO_2$ equivalent/ton epsilon-caprolactam, even more preferably less than 2.5 ton $CO_2$ equivalent/ton epsilon-caprolactam, most preferably less than 2 ton $CO_2$ equivalent/ton epsilon-caprolactam (based on data originating from ecoinvent version 3.7.1; location: Europe).

BRIEF DESCRIPTION OF THE DRAWINGS

In the following, the invention will be described with reference to the Figures, which depict certain embodiments of the invention. The invention, however, is as defined in the claims and as generally described herein. It should not be limited to the embodiments shown for illustrative purposes in the Figures below.

FIG. 2 illustrates three embodiments of the Nylon 6 pre-concentration step a) of the process of the invention, in which the Nylon 6-containing multi-component material is extracted with organic solvent(s) to obtain a pre-treated Nylon 6 containing phase, which is enriched in Nylon 6.

FIG. 2a depicts an embodiment of the Nylon 6 pre-concentration step a) of the process of the invention, in which non-Nylon 6 compounds are preferentially extracted from the Nylon 6-containing multi-component material to obtain the pre-concentrated Nylon 6-containing material, which is enriched in Nylon 6.

FIG. 2b depicts an embodiment of the Nylon 6 pre-concentration step a) of the process of the invention, in which Nylon 6 is preferentially extracted from the Nylon 6-containing multi-component material to obtain the pre-concentrated Nylon 6-containing material, which is enriched in Nylon 6.

FIG. 2c depicts an embodiment of the Nylon 6 pre-concentration step a) of the process of the invention, in which extraction of non-Nylon 6 compounds from the Nylon 6-containing multi-component material is combined with the extraction of Nylon 6 from the resulting Nylon 6-containing phase, which is enriched in Nylon 6 to obtain a Nylon 6-containing phase, which is further enriched in Nylon 6.

DETAILED DESCRIPTION OF THE DRAWINGS

Figure 1:
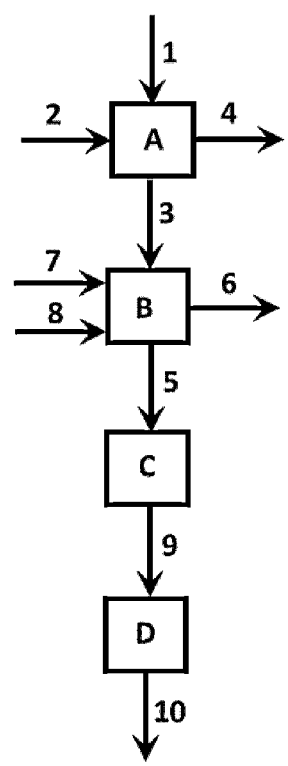
FIG. 1 is a schematic of the process of the invention comprising processing steps performed in a Nylon 6-pre-concentration section, a depolymerization section, a recovery section and a purification section.

The process of the invention is schematically illustrated in FIG. 1. The process comprises the following sections:

Nylon 6-pre-concentration section [A], in which the Nylon 6-containing multi-component material [1] is treated with an (organic) solvent [2] to obtain a pre-concentrated Nylon 6-containing material, which is enriched in Nylon 6 [3] and a second phase that comprises non-Nylon 6-compounds [4];

Depolymerization section [B], in which the pre-treated Nylon 6, which is enriched in Nylon 6 [3] is depolymerized to epsilon-caprolactam, that is discharged as an epsilon-caprolactam-containing product vapor stream [5]. In addition, residual material [6] is discharged. Superheated steam [7] and optionally catalyst [8] are charged to the depolymerization section [B];

Recovery section [C], in which crude epsilon-caprolactam [9] is recovered from the epsilon-caprolactam-containing product vapor stream [5] that is discharged from the depolymerization section [B]; and Purification section [D], in which crude epsilon-caprolactam [9] that is discharged from the recovery section [C] is purified to yield high purity epsilon-caprolactam [10].

FIG. 2a depicts an embodiment of an extraction in a Nylon 6-pre-concentration section [A"], in which the Nylon 6-containing multi-component material [1'] is treated with a solvent [2'] that preferentially extracts non-Nylon 6 compounds from the Nylon 6-containing multi-component material [1'] to obtain a pre-concentrated Nylon 6-containing material, which is enriched in Nylon 6 [3'] and a second phase [4'] that is enriched in non-Nylon 6-compounds.

FIG. 2b depicts an embodiment of an extraction in a Nylon 6-pre-concentration section [A"], in which the Nylon 6-containing multi-component material [1"] is treated with a solvent [2"] that preferentially extracts Nylon 6 from the Nylon 6-containing multi-component material [1"] to obtain a pre-concentrated Nylon 6-containing material, which is enriched in Nylon 6 [3"] and a second phase [4"] that is enriched in non-Nylon 6-compounds.

FIG. 2c depicts an embodiment of an extraction in a first Nylon 6-pre-concentration section [A'''], in which the Nylon 6-containing multi-component material [1'''] is treated with a solvent [2'''] that preferentially extracts non-Nylon 6 compounds from the Nylon 6-containing multi-component material [1'''] to obtain a pre-treated Nylon 6 containing phase, which is enriched in Nylon 6 [3'''] and a second phase [4'''] that is enriched in non-Nylon 6-compounds. In a second Nylon 6-pre-concentration section [A''''], the pre-concentrated Nylon 6-containing material, which is enriched in Nylon 6 [3'''] is treated with a second solvent [2''''] that preferentially extracts Nylon 6 from the pre-concentrated Nylon 6-containing material, which is enriched in Nylon 6 [3'''] to obtain a pre-treated Nylon 6 comprising phase, which is further enriched in Nylon 6 [3''''] and a further phase [4''''] that is enriched in non-Nylon 6-compounds.

The present invention is illustrated by, but not intended to be limited to, the following examples.

EXAMPLES

The starting material that was used in the Examples 1 and 2 and 4 and in the Comparative Examples were waste multi-layered packaging films, comprising layers of polyethylene and Nylon 6. The Nylon 6 layers were buried in the used waste multi-layered packaging films, i.e., sandwiched in between other layers and therefore not well accessible.

The Nylon 6-pre-concentration step a) of the waste multi-layered packaging films can be performed as described in EP0849312 or in DE102016015198, wherein polyethylene is selectively dissolved at elevated temperatures in an organic solvent, e.g., white spirit (Sigma-Aldrich; CAS number 68551-17-7) or methylcyclohexane, whereby the resulting mixture comprises undissolved Nylon 6 and an organic solution comprising organic solvent and dissolved polyethylene. Undissolved Nylon 6 material is obtained after separation of the organic solution from the resulting mixture. The resulting undissolved Nylon 6 material can be dried and optionally densified by melting under nitrogen and subsequently converted into solid particles that are enriched in Nylon 6 as compared to the Nylon 6-containing multi-component starting material.

To determine the quality of the obtained epsilon-caprolactam, the following parameters were measured: The permanganate absorption number of epsilon-caprolactam was determined (PAN: ISO 8660—Plastics—Determination of permanganate absorption number of caprolactam—Spectometric method, second edition ISO 8660; 2002). Moreover the absorbance at wavelength of 290 nm was measured (E290: ISO 7059—Caprolactam for industrial use—Determination of absorbance at a wavelength of 290 nm; 1982). Additionally, the volatile bases content was determined (Volatile bases (VB): ISO 8661—Caprolactam for industrial use—Determination of volatile bases content—Titrimetric method after distillation, 1988). Finally, the alkalinity or acidity is determined by titration at a temperature of 25° C. using a Tashiro indicator in a 1:2 ratio of 0.1 wt./$v_{Ethanol \%}$ Methylene blue:0.1 wt./$v_{Ethanol \%}$ Methyl red, which is grey at its end point. A flask containing water and indicator is first titrated to grey, then X grams of an aqueous epsilon-caprolactam solution containing Y wt. % epsilon-caprolactam (as determined by refractive index) is added and the solution is titrated back to grey using a 0.01 N $H_2SO_4$ solution (in case the solution is alkaline) or a 0.01 N NaOH solution (in case the solution is acidic).

Alkalinity is then given by:

$$\text{Alkalinity}(\text{mmol/kg epsilon-caprolactam}) = v * t * 1000/(X * Y)$$

Where:
v=volume of $H_2SO_4$ solution added (ml)
t=normality of $H_2SO_4$ solution (=0.01 N)
X=weight of sample (g)
Y=concentration epsilon-caprolactam (wt. %)

Acidity is then given by:

$$\text{Acidity}(\text{mmol/kg epsilon-caprolactam}) = v * t * 1000/(X * Y)$$

Where:
v=volume of NaOH solution added (ml)
t=normality of NaOH solution (=0.01 N)
X=weight of sample (g)
Y=concentration epsilon-caprolactam (wt. %)

epsilon-caprolactam, that can be used for all major polymerization applications, without dilution with purer qualities of epsilon-caprolactam, fulfils all of the following specifications:
PAN: max. 5
E290: max. 0.05
VB: max. 0.5 mmol/kg
Alkalinity: max. 0.1 mmol/kg
Acidity: max. 0.1 mmol/kg Example 1

Depolymerization of Nylon 6 and Recovery of Epsilon-Caprolactam.

The material used for depolymerization and the further processing steps as described below can be any Nylon 6-containing multi-component material or derivative thereof. The particular material that was used in the following examples was enriched in Nylon 6 as compared to Nylon 6-containing multi-component starting material and was prepared as described above from waste multi-layered packaging films.

The enriched in Nylon 6 starting material was shaped into pearl-like solid particles (diameter: 3 to 4 mm). The polyethylene content in the undissolved Nylon 6 material was about 1 wt. % as determined by TGA (Thermal Gravimetric Analysis).

In step b), 33.6 g of the pearl-like solid particles and 9.8 grams of 20 wt. % phosphoric acid were charged to a Premex high pressure autoclave. First, the reactor content was heated under nitrogen and subsequently superheated steam was injected continuously at a rate of 4 grams per minute during the 120-minute reaction. The temperature and the pressure in the reactor were maintained at 260° C. and 0.11 MPa, respectively. During the reaction a vapor stream was continuously discharged from the reactor.

In step c), to recover crude epsilon-caprolactam from the obtained vapor, the latter was cooled to 20° C. The condensate that composed of on average 28.3 grams of epsilon-caprolactam, most of the remainder being water, was concentrated by evaporation in a rotavap (rotary evaporator) that was operated under vacuum (9.5 kPa; water bath temperature was ca. 65° C.) to an epsilon-caprolactam concentration of on average 49.6 wt. %. (The resulting mixture, crude epsilon-caprolactam, is the mixture to be purified.)

Step b) and step c) were repeated five times. The five mixtures were combined and the resulting solution was used as stock solution in the following Examples and Comparative Experiments.

This EXAMPLE shows that crude epsilon-caprolactam can be obtained in good yield and without operational issues by depolymerization of Nylon 6 that originates from discarded Nylon 6 waste multi-layered packaging films.

Example 2

Purification by Extraction, Caustic Wash, Reextraction, Oxidation and Distillation.

In step d)(i) 70 gram of crude epsilon-caprolactam that was obtained in EXAMPLE 1 was extracted one time with 100 gram and nine times with 50 gram solvent mixture MIBC/cyclohexane (50 wt. %:50 wt. %) at 25° C. The ten resulting epsilon-caprolactam phases comprising solvent mixtures were combined and washed with 7 gram aqueous caustic solution (2 wt. %). Subsequently, the washed epsilon-caprolactam comprising solvent mixture was extracted six times with 50 gram of water at 25° C. The six resulting aqueous epsilon-caprolactam phases were combined. Water and residual solvent mixture were distilled out of the aqueous epsilon-caprolactam phase whereby a concentrated epsilon-caprolactam solution with a water content of 50 wt. % was obtained. The resulting mixture was treated with 0.2 wt. % $KMnO_4$ with regard to epsilon-caprolactam at 50° C. for 2 hours. The solids formed were then removed from the oxidized reaction product by means of a filtration. 75 mmol of aqueous sodium hydroxide per kg epsilon-caprolactam was then added to the resulting aqueous epsilon-caprolactam solution.

In step d)(ii), a distillative removal of water and impurities with lower or higher boiling points than epsilon-caprolactam was performed. Subsequently, water and impurities with lower boiling points than epsilon-caprolactam were removed as top products by distillation under reduced pressure in a batch-wise operated distillation set-up. Finally, purified epsilon-caprolactam was recovered as top product at 300 Pa, while the impurities with higher boiling points compared to epsilon-caprolactam remained as bottom product in the distillation set-up. The specifications of the purified epsilon-caprolactam were:

PAN: 5
E290: 0.023
VB: 0.167
Alkalinity: 0.044

From this EXAMPLE, it can be concluded that purified epsilon-caprolactam that meets the required specifications for major polymerization applications can be obtained from depolymerized waste multi-layered packaging film pieces from which polyethylene was removed by extraction and was purified by extraction with an organic solvent, oxidation and distillation.

Comparative Experiment 1

Purification by Distillation.

0.75 mmol of aqueous sodium hydroxide per kg epsilon-caprolactam was added to 35 gram of crude epsilon-caprolactam that was obtained in EXAMPLE 1. This mixture was then distilled according to the procedure described in EXAMPLE 2. The specifications of the purified epsilon-caprolactam were:

PAN: 73.5
E290: 0.531
VB: 0.718
Acidity: 7.643

This COMPARATIVE EXPERIMENT shows that the quality of epsilon-caprolactam that is obtained from depolymerization of waste multi-layered packaging film pieces from which polyethylene was removed by extraction and was purified by distillation is very poor as it does not meet any of the required specifications for major polymerization applications.

Comparative Experiment 2

Purification by Oxidation and Distillation.

35 gram of crude epsilon-caprolactam that was obtained in EXAMPLE 1 was treated with 0.2 wt. % $KMnO_4$ with regard to epsilon-caprolactam at 50° C. for 2 hours. The solids formed were then removed from the oxidized reaction product by means of a filtration. 0.75 mmol of aqueous sodium hydroxide per kg epsilon-caprolactam was then added to the resulting aqueous epsilon-caprolactam solution. This mixture was then distilled according to the procedure described in EXAMPLE 2. The specifications of the purified epsilon-caprolactam were:

PAN: 11.7
E290: 0.324
VB: 0.657
Acidity: 2.991

This COMPARATIVE EXPERIMENT shows that the quality of epsilon-caprolactam that is obtained from depolymerization of waste multi-layered packaging film pieces from which polyethylene was removed by extraction and was purified by oxidation and distillation is very poor as it does not meet any of the required specifications for major polymerization applications.

Comparative Experiment 3

Purification by Extraction, Caustic Wash, and Reextraction.

70 gram of crude epsilon-caprolactam that was obtained in EXAMPLE 1 was extracted one time with 100 gram and nine times with 50 gram solvent mixture MIBC/cyclohexane (50 wt. %:50 wt. %) at 50° C. The ten resulting epsilon-caprolactam phases comprising solvent mixtures were combined and washed with 7 gram aqueous caustic solution (2 wt. %). Subsequently, the washed epsilon-caprolactam comprising solvent mixture was reextracted six times with 50 g of water at 25° C. The six resulting aqueous epsilon-caprolactam phases were combined. Water and residual solvent mixture were distilled out of the aqueous epsilon-caprolactam phase whereby a concentrated epsilon-caprolactam solution with an epsilon-caprolactam content of 50.4 wt. % was obtained. The specifications of the purified epsilon-caprolactam were:

PAN: 82
E290: 1.2

This COMPARATIVE EXPERIMENT shows that the quality of epsilon-caprolactam that is obtained from depolymerization of waste multi-layered packaging film pieces from which polyethylene was removed by extraction and was purified by extraction and reextraction is very poor as it does not meet all the required specifications for major polymerization applications.

Comparative Experiment 4

Purification by extraction, caustic wash, reextraction and oxidation. The concentrated epsilon-caprolactam solution with an epsilon-caprolactam content of 50.4 wt. % that was obtained in COMPARATIVE EXPERIMENT 3 was treated with 0.04 wt. % $KMnO_4$ with regard to epsilon-caprolactam at 50° C. for 2 hours. The solids formed were then removed from the oxidized reaction product by means of a filtration. The specifications of the purified epsilon-caprolactam were:

PAN: 83
E290: 3.01

This COMPARATIVE EXPERIMENT shows that the quality of epsilon-caprolactam that is obtained from depolymerization of waste multi-layered packaging film pieces from which polyethylene was removed by extraction and was purified by extraction, reextraction and oxidation is very poor as it does not meet all the required specifications for major polymerization applications.

Example 3

Calculation of Product Carbon Footprint of Purified Epsilon-Caprolactam

A continuous process according to the invention for the production of purified epsilon-caprolactam from waste multi-layered packaging films, comprising layers of polyethylene and Nylon 6 was simulated. The Nylon 6 content of these waste multi-layered packaging films, comprising layers of polyethylene and Nylon 6 was 20 wt. %.

The process included:
Cutting waste multi-layered packaging films, comprising layers of polyethylene and Nylon 6 in small pieces;
Washing with water of the small pieces of waste multi-layered packaging films, comprising layers of polyethylene and Nylon 6;
Drying by centrifugation of the washed small pieces of waste multi-layered packaging films, comprising layers of polyethylene and Nylon 6;
Extraction of polyethylene with white spirit;
Separation of non-dissolved solid pre-concentrated Nylon 6-containing material by centrifugation;
Washing of non-dissolved solid pre-concentrated Nylon 6-containing material with water;

Separation of washed non-dissolved solid pre-concentrated Nylon 6-containing material and aqueous extract by centrifugation;

Decolorization of the polyethylene comprising white spirit solution by treatment with active carbon;

Recovery of polyethylene from the polyethylene comprising white spirit solution by cooling and partial evaporation of the white spirit;

Melting and pelletization of recovered polyethylene;

Melting and pelletization of washed non-dissolved solid pre-concentrated Nylon 6-containing material;

Depolymerization of Nylon 6 in the pelletized Nylon 6-containing material under influence of $H_3PO_4$ and superheated steam;

Recovery of crude epsilon-caprolactam by partial condensation of vapors discharged from depolymerization reactor;

Evaporative concentration of crude epsilon-caprolactam to 80 wt. % epsilon-caprolactam;

Counter-current extraction of concentrated crude epsilon-caprolactam with benzene;

Washing of organic extract with diluted caustic solution;

Counter-current extraction of washed organic extract with water;

Evaporative concentration of aqueous extract;

Oxidation of the concentrated extract with $KMnO_4$ and then filtration of the oxidized reaction product to remove solids formed;

Addition of caustic;

Recovery of pure epsilon-caprolactam by vacuum distillation.

The main products of this process are polyethylene and pure epsilon-caprolactam. The pure epsilon-caprolactam recovery yield is about 0.8 kg pure epsilon-caprolactam per kg Nylon 6 in the waste multi-layered packaging films, comprising layers of polyethylene and Nylon 6. The obtained by-products are incinerated with energy recovery.

The product carbon footprint of purified epsilon-caprolactam was calculated based on the consumption figures of raw materials, and utilities of the above described process are based on data originating from ecoinvent version 3.7.1. The distribution of the environmental impact between the products purified epsilon-caprolactam and polyethylene in the Nylon 6-pre-concentration section was based on the weight ratio of these products.

The outcome revealed that the product carbon footprint of purified epsilon-caprolactam obtained from multi-layered packaging films, comprising layers of polyethylene and Nylon 6 is less than 2 ton $CO_2$ eq./ton of epsilon-caprolactam (location: Europe).

Example 4

Depolymerization of Nylon 6 and Recovery of Epsilon-Caprolactam.

The material used for depolymerization and the further processing steps as described below was enriched in Nylon 6 as compared to Nylon 6-containing multi-component starting material and was prepared as described above from waste multi-layered packaging films. The enriched in Nylon 6 starting material was shaped into pearl-like solid particles (diameter: 3 to 4 mm). The polyethylene content in the undissolved Nylon 6 material was about 1 wt. % as determined by TGA (Thermal Gravimetric Analysis).

In step b), 33.6 g of the pearl-like solid particles and 9.8 grams of 20 wt. % phosphoric acid were charged to a Premex high pressure autoclave. First, the reactor content was heated under nitrogen and subsequently superheated steam was injected continuously at a rate of 2.7 grams per minute during the 135-minute reaction. The temperature and the pressure in the reactor were maintained at 260° C. and 0.11 MPa, respectively. During the reaction a vapor stream was continuously discharged from the reactor.

In step c), to recover crude epsilon-caprolactam from the obtained vapor, the latter was cooled to 20° C. The condensate was composed of 26.1 grams of epsilon-caprolactam, most of the remainder being water.

Step b) and step c) were repeated by following the same procedure except that now 9.7 grams of 20 wt. % phosphoric acid were charged to a Premex high pressure autoclave and that the obtained condensate was composed of 26.9 grams of epsilon-caprolactam.

The two epsilon-caprolactam containing condensates were concentrated by evaporation in a rotavap (rotary evaporator) that was operated under vacuum (9.5 kPa; water bath temperature was ca. 65° C.) and thereafter combined to an epsilon-caprolactam concentration of 79.6 wt. %. The resulting stock solution, crude epsilon-caprolactam, is the mixture to be purified (see EXAMPLE 5).

The specifications of the crude epsilon-caprolactam were:
PAN: 280
E290: 2.14

This EXAMPLE shows that crude epsilon-caprolactam can be obtained in good yield and without operational issues by depolymerization of Nylon 6 that originates from discarded Nylon 6 waste multi-layered packaging films.

Example 5

Purification by Extraction, Reextraction, Oxidation and Distillation.

In step d)(i) 43.4 gram of crude epsilon-caprolactam that was obtained in EXAMPLE 4 was diluted to 68.9 wt. % by adding 6.7 g of water, the obtained solution was extracted one time with 77.5 gram and four times with 50 gram benzene at 25° C. The resulting organic extracts were combined and concentrated by evaporation in a rotavap that was operated under vacuum (9.5 kPa; water bath temperature was ca. 65° C.) to an epsilon-caprolactam concentration of about 24.5 wt. %. Subsequently, the epsilon-caprolactam comprising concentrated extract was 3 times batch-wise extracted with 25 gram water at a temperature of ca. 25° C. The three resulting aqueous epsilon-caprolactam phases were combined. Water and residual solvent mixture were distilled out of the aqueous epsilon-caprolactam phase whereby a concentrated epsilon-caprolactam solution with a water content of 49.5 wt. % was obtained. The specifications of the aqueous epsilon-caprolactam solution after reextraction were:
PAN: 83
E290: 1.15

The resulting mixture was treated with 0.2 wt. % $KMnO_4$ with regard to epsilon-caprolactam at 50° C. for 2 hours. The solids formed were then removed from the oxidized reaction product by means of a filtration. 75 mmol of aqueous sodium hydroxide per kg epsilon-caprolactam was then added to the aqueous epsilon-caprolactam solution after oxidation. This mixture was then distilled according to the procedure described in EXAMPLE 2. The specifications of the purified epsilon-caprolactam were:
PAN: <5
E290: <0.05
VB: <0.5 mmol/kg
Alkalinity: <0.1 mmol/kg
Acidity: <0.1 mmol/kg From this EXAMPLE, it can be concluded that purified epsilon-caprolactam that meets the required specifications for major polymerization applications can be obtained from depolymerized waste multi-layered packaging film pieces from which polyethylene was removed by extraction and was purified by extraction with benzene, reextraction with water, oxidation and distillation.

While the present invention has been illustrated by means of several preferred embodiments, one of ordinary skill in the art will recognize that changes, modifications including conversion into a continuous mode of operation, and improvements can be made while still remaining within the scope and spirit of the present invention. Accordingly, no limitation upon the invention is intended, except as set forth in the appended claims.

The invention claimed is:

1. A process for recovering purified epsilon-caprolactam derived from a Nylon 6-containing multi-component material in an industrial scale plant with a production capacity for epsilon-caprolactam of at least 500 tons/year if operated all the time, wherein the plant comprises
   a Nylon 6-depolymerization section comprising one or more depolymerization reactors that are operated in at least one of series and parallel,
   a recovery section comprising one or more condensers, and
   a purification section comprising one or more pieces of extraction equipment, one or more pieces of solvent switch equipment, and one or more pieces of distillation equipment,
and wherein the process comprises the steps of:
   a) providing a pre-concentrated Nylon 6-containing material that has been obtained by extracting a Nylon 6-containing multi-component material with one or more organic solvents to obtain a solid pre-concentrated Nylon 6-containing material, which is enriched in Nylon 6 as compared to the Nylon 6-containing multi-component material;
   b) depolymerizing the pre-concentrated Nylon 6-containing material in the depolymerization section in the presence of water to obtain a vapor stream comprising water and epsilon-caprolactam in a weight to weight ratio of 2:1 to 15:1;
   c) recovering crude epsilon-caprolactam from said vapor stream in the recovery section; and
   d) purifying said crude epsilon-caprolactam in the purification section to obtain purified epsilon-caprolactam,
wherein
the purification comprises the steps of
   (i) extracting the crude epsilon-caprolactam with an organic solvent, whereby an aqueous phase and an organic phase are obtained, and wherein the organic phase comprises the organic solvent, epsilon-caprolactam and impurities;
   (ii) switching the solvent by replacing the organic solvent at least partially with water, whereby an aqueous phase comprising water, epsilon-caprolactam and impurities with lower- or higher-boiling points than epsilon-caprolactam is obtained and wherein the solvent switch step (ii) is selected from a process based on back-extraction with water, and a process based on solvent swap distillation, in which the organic solvent is distilled off and water is charged; and
   (iii) obtaining purified epsilon-caprolactam by distillative removal of impurities with lower- or higher-boiling points than epsilon-caprolactam;
wherein after step d)(i), the organic phase obtained in step d)(i) is washed with water or with an aqueous alkaline solution;
wherein step d)(ii) is followed by oxidation by an oxidant selected from potassium permanganate, sodium permanganate and hydrogen peroxide; and
wherein the Nylon 6-containing multi-component material is a multi-layer packaging film that is a thin sheet with a thickness of less than 1 mm and contains at least one layer comprising or consisting of Nylon 6 and at least one layer not comprising Nylon 6, wherein the at least one layer comprising or consisting of Nylon 6 is sandwiched in between two or more layers not comprising Nylon 6.

2. The process according to claim 1, wherein the weight fraction of Nylon 6 in the Nylon 6-containing multi-component material ranges from 1 wt. % to 75 wt. %, based on the total weight of the Nylon 6-containing multi-component material.

3. The process according to claim 1, wherein the extracting in step a) comprises the steps of
   (i) adding the one or more organic solvents to the Nylon 6-containing multi-component material;
   (ii) performing a phase separation to obtain a liquid extract phase comprising solvent and dissolved components from the Nylon 6-containing multi-component material and an at least partially solid phase comprising undissolved components of the Nylon 6-containing multi-component material and optionally solvent;
   (iii) removing the solvent from the liquid extract phase and, if present therein, also from the at least partially solid phase to obtain two solid phases, one of which is the pre-concentrated Nylon 6-containing material that is enriched in Nylon 6 as compared to the Nylon 6-containing multi-component material that is used as starting material.

4. The process according to claim 1, wherein an organic solvent is used for the extracting in step a) that preferentially dissolves at least one of non-Nylon 6 compounds from the Nylon 6-containing multi-component material and Nylon 6 from the Nylon 6-containing multi-component material.

5. The process according to claim 1, further comprising at least one additional step selected from:
   (i) prior to the extracting in step a) the Nylon 6-containing multi-component material has been subjected to at least one additional pre-treatment step comprising a washing step and a mechanical size reduction step; and
   (ii) wherein the depolymerization of the pre-concentrated Nylon 6-containing material in step b) is conducted at a temperature ranging from 180° C. to 400° C.; and
   (iii) wherein the water present in step b) is in the form of steam, which is preferably charged to the depolymerization section in step b) as super-heated steam having a temperature ranging from 220° C. to 575° C.

6. The process according to claim 1, wherein the depolymerization of the pre-concentrated Nylon 6-containing material in step b) is carried out in the absence or presence of a catalyst, wherein the catalyst is selected from an acid and a base catalyst, the acid catalyst being selected from the group consisting of orthophosphoric acid, boric acid, sulfuric acid, organic acid, organic sulfonic acid, salts of the aforementioned acids, $Al_2O_3$ and $SiO_2$, and combinations thereof, and the base catalyst being selected from the group consisting of alkali hydroxide, alkali salt, alkaline earth hydroxide and alkaline earth salts, organic bases and solid bases, and combinations thereof.

7. The process according to claim 1, wherein
prior to the distillative removal in step d)(iii), an alkali metal hydroxide, is added.

8. The process according to claim 1, wherein prior to the distillative removal in step d)(iii) an aqueous phase comprising water, epsilon-caprolactam and impurities with lower or higher boiling points than epsilon-caprolactam is obtained by
at least partially replacing the organic solvent with water, and wherein the solvent replacement step is selected from a process based on reextraction with water, and a process based on solvent replacement distillation, in which the organic solvent is distilled off and water is charged.

9. The process according to claim 1, wherein in the purification section used in step d) further comprises an addition of crude epsilon-caprolactam obtained from a Beckmann rearrangement of cyclohexanone oxime with the crude epsilon-caprolactam that is recovered in step c).

10. The process according to claim 2, wherein the weight fraction of Nylon 6 in the Nylon 6-containing multi-component material ranges from 1 wt. % to 60 wt. % based on the total weight of the Nylon 6-containing multi-component material.

11. The process according to claim 2, wherein the weight fraction of Nylon 6 in the Nylon 6-containing multi-component material ranges from 2 wt. % to 35 wt. %.

12. The process according to claim 2, wherein the weight fraction of Nylon 6 in the Nylon 6-containing multi-component material ranges from 3 wt. % to 25 wt. %.

13. The process according to claim 5, wherein the depolymerization of the pre-concentrated Nylon 6-containing material in step b) is conducted at a temperature ranging from 200° C. to 350° C.

14. The process according to claim 5, wherein the depolymerization of the pre-concentrated Nylon 6-containing material in step b) is conducted at a temperature ranging from 220° C. to 340° C.

15. The process according to claim 5, wherein the depolymerization of the pre-concentrated Nylon 6-containing material in step b) is conducted at a temperature ranging from 240° C. to 325° C.

16. The process of claim 5, wherein the water present in step b) is in the form of steam, which is preferably charged to the depolymerization section in step b) as super-heated steam having a temperature ranging from 275° C. to 500° C.

17. The process of claim 6, wherein the acid catalyst is orthophosphoric acid.

18. The process of claim 6, wherein the base catalyst is selected from the group consisting of: sodium hydroxide, potassium hydroxide, sodium carbonate, potassium carbonate, sodium hydrogen carbonate, and potassium hydrogen carbonate.

19. The process of claim 7, wherein the alkali metal hydroxide is NaOH.

20. The process according to claim 8, wherein the step of at least partially replacing the organic solvent with water, further comprises one or more of the following steps:
a. oxidation by an oxidant selected from potassium permanganate, sodium permanganate and hydrogen peroxide;
b. treatment with an acidic cation exchange resin and/or a basic anion exchange resin; and
c. hydrogenation in the presence of a hydrogenation catalyst selected from Raney nickel, nickel on silica, nickel on aluminum oxide, ruthenium on aluminum oxide, rhodium on aluminum oxide, platinum on carbon and palladium on carbon.

* * * * *